US010653766B2

(12) United States Patent
Cheminay et al.

(10) Patent No.: US 10,653,766 B2
(45) Date of Patent: May 19, 2020

(54) USE OF OIL AND WATER EMULSIONS FOR INCREASING B CELL RESPONSES WITH MODIFIED VACCINIA ANKARA VIRUS

(71) Applicant: Bavarian Nordic A/S, Kvistgaard (DK)

(72) Inventors: Cédric Cheminay, Munich (DE); Robin Steigerwald, Munich (DE); Ariane Volkmann, Andechs (DE)

(73) Assignee: Bavarian Nordic A/S, Kvistgaard (DK)

( * ) Notice: Subject to any disclaimer, the term of this patent is extended or adjusted under 35 U.S.C. 154(b) by 36 days.

(21) Appl. No.: 15/125,388

(22) PCT Filed: Mar. 12, 2015

(86) PCT No.: PCT/EP2015/055239
§ 371 (c)(1),
(2) Date: Sep. 12, 2016

(87) PCT Pub. No.: WO2015/136056
PCT Pub. Date: Sep. 17, 2015

(65) Prior Publication Data
US 2017/0128561 A1    May 11, 2017

Related U.S. Application Data

(60) Provisional application No. 61/951,672, filed on Mar. 12, 2014.

(51) Int. Cl.
| | |
|---|---|
| *A61K 39/00* | (2006.01) |
| *A61K 39/21* | (2006.01) |
| *A61K 39/02* | (2006.01) |
| *A61K 38/00* | (2006.01) |
| *A61K 39/395* | (2006.01) |
| *A61K 39/12* | (2006.01) |
| *A61K 39/285* | (2006.01) |
| *A61K 39/155* | (2006.01) |

(52) U.S. Cl.
CPC ............ *A61K 39/12* (2013.01); *A61K 39/155* (2013.01); *A61K 39/285* (2013.01); *A61K 2039/5254* (2013.01); *A61K 2039/5256* (2013.01); *A61K 2039/55566* (2013.01); *A61K 2039/57* (2013.01); *C12N 2710/24121* (2013.01); *C12N 2710/24134* (2013.01); *C12N 2710/24143* (2013.01); *C12N 2760/18534* (2013.01); *C12N 2770/24134* (2013.01); *Y02A 50/388* (2018.01)

(58) Field of Classification Search
CPC .......................... A61K 39/12; A61K 2039/53; A61K 39/0011; C07K 14/005; C07K 2319/00
See application file for complete search history.

(56) References Cited

U.S. PATENT DOCUMENTS

| | | | |
|---|---|---|---|
| 4,650,677 | A | 3/1987 | Roerink |
| 5,690,942 | A | 11/1997 | Hjorth |
| 5,718,904 | A | 2/1998 | Hjorth |
| 2010/0221282 | A1 | 9/2010 | Loosmore et al. |

FOREIGN PATENT DOCUMENTS

| | | | |
|---|---|---|---|
| WO | WO 03/048184 A2 | | 6/2003 |
| WO | WO 03/053463 A2 | | 7/2003 |
| WO | WO 2005/099750 A2 | | 10/2005 |
| WO | WO 2006/089690 A1 | | 8/2006 |
| WO | WO 2007/016715 A2 | | 2/2007 |
| WO | WO 2011/043962 A2 | | 4/2011 |
| WO | WO2012/040474 | * | 3/2012 |
| WO | WO 2012/040474 A2 | | 3/2012 |
| WO | WO2012/042279 | * | 4/2012 |
| WO | WO 2012/042279 A2 | | 4/2012 |
| WO | WO2012042279 | * | 4/2012 |
| WO | WO 2014/037124 A1 | | 3/2014 |
| WO | WO 2014/043535 A1 | | 3/2014 |
| WO | WO 2014/062778 A1 | | 4/2014 |
| WO | WO 2014/139687 A1 | | 9/2014 |

OTHER PUBLICATIONS

Vollmar et al., "Safety and immunogenicity of IMVAMUNE, a promising candidate as a third generation smallpox vaccine",Vaccine, 2006, 24(12):2065-2070.*
Frey et al., "Phase II randomized, double-blinded comparison of a single high dose (5 x 10sup8 TCID50) of modified vaccinia ankara compared to a standard dose (1 x 10sup8 TCID50) in Healthy vaccinia-naive individuals", Vaccine, 2014, 32(23):2732-2739.*
Baur et al., Immediate-Early Expression of a Recombinant Antigen by Modified Vaccinia Virus Ankara Breaks the Immunodominance of Strong Vector-Specific B8R Antigen in Acute and Memory CD8 T-Cell Responses. J. Virol. 84:8743-52 (2010).
Cochran et al., In Vitro Mutagenesis of the Promoter Region for a Vaccinia Virus Gene: Evidence for Tandem Early and Late Regulatory Signals. J Viral 54: 30-37 (1985).
Douglas et al., Tailoring subunit vaccine immunogenicity: Maximizing antibody and T cell responses by using combinations of adenovirus, poxvirus and protein-adjuvant vaccines against Plasmodium falciparum MSP1. Vaccine 28:7167-7178 (2010).
Dupuis et al., SEPPIC Vaccine Adjuvants for Poultry. Ann N Y Arad Sci 1081: 202-5 (2006).
Ganne et al., Enhancement of the efficacy of a replication-defective adenovirus-vectored vaccine by the addition of oil adjuvants. Vaccine 12:1190-1196 (1994).

(Continued)

*Primary Examiner* — Barry A Chestnut

(57) ABSTRACT

The invention relates to compositions, uses, and methods for inducing an immune response against a vaccinia virus. The addition of an oil and water emulsion to MVA can vastly increase the B cell response and particularly neutralizing antibodies against vaccinia virus and encoded recombinant antigens. Thus, the addition of an oil and water emulsion to MVA can increase the protective immune response. The invention encompasses administering a dose of an MVA in an oil and water emulsion to an animal, especially a human.

28 Claims, 19 Drawing Sheets

Specification includes a Sequence Listing.

(56) References Cited

OTHER PUBLICATIONS

Garza et al., Evaluation of the efficacy of modified vaccinia Ankara (MVA)/IMVAMUNE® against aerosolized rabbitpox virus in a rabbit model . Vaccine 27, 5496-5504 (2009).
Genton et al., Evaluation of the efficacy of modified vaccinia Ankara (MVA)/IMVAMUNE® against aerosolized rabbitpox virus in a rabbit model . Vaccine 22:30-41 (2003).
Harrer et al. ,Therapeutic vaccination of HIV-1-infected patients on HAART with a recombinant HIV-1 nef-expressing MVA: safety, immunogenicity and influence on viral load during treatment interruption. Antivir. Ther. 10, 285-300 (2005).
Krempelhuber et al., A randomized, double-blind, dose-finding Phase II study to evaluate immunogenicity and safety of the third generation smallpox vaccine candidate IMVAMUNE®. Vaccine 28:1209-16 (2010).
Kyriakis et al., Safety, immunogenicity and efficacy of poxvirus-based vector vaccines expressing the haemagglutinin gene of a highly pathogenic H5N1 avian influenza virus in pigs. Vaccine 27:2258-2264 (2009).
Mandl et al., Immunotherapy with MVA-BN®-HER2 induces HER-2-specific Th1 immunity and alters the intratumoral balance of effector and regulatory T cells. Cancer Immunol. Immunother. (2011).
Meyer et al., A phase I vaccination study with tyrosinase in patients with stage II melanoma using recombinant modified vaccinia virus Ankara (MVA-hTyr). Cancer Immunol. Immunother. 54, 453-467 (2005).
Moreira et al., Modulation of adaptive immunity by different adjuvant-antigen combinations in mice lacking Nod2. Vaccine 26:5808-5813 (2008).
Samuelsson et al., Survival of lethal poxvirus infection in mice depends on TLR9, and therapeutic vaccination provides protection. J. Clin. Invest 118, 1776-1784 (2008.
Schafer et al., Pre-Clinical Efficacy and Safety of Experimental Vaccines Based on Non-Replicating Vaccinia Vectors against Yellow Fever . PLoS One. 6(9):e24505 (2011).
Smith and Moss, Infectious poxvirus vectors have capacity for at least 25 000 base pairs of foreign DNA . Gene 25, 21-28 (1983).
Stittelaar et al., Modified Vaccinia Virus Ankara Protects Macaques against Respiratory Challenge with Monkeypox Virus. J. Virol. 79, 7845-7851 (2005).
Suter et al., Modified vaccinia Ankara strains with identical coding sequences actually represent complex mixtures of viruses that determine the biological properties of each strain. Vaccine 27, 7442-7450 (2009).
Tekes et al., Genome Organization and Reverse Genetic Analysis of a Type I Feline Coronavirus. J. Viral. 82, 1851-1859 (2010).
Timm et al., Genetic stability of recombinant MVA-BN. Vaccine 24, 4618-4621 (2006).
Vollmar et al., Safety and immunogenicity of IMVAMUNE, a promising candidate as a third generation smallpox vaccine. Vaccine 24, 2065-2070 (2006).
Warimwe et al., Immunogenicity and efficacy of a chimpanzee adenovirus-vectored Rift Valley Fever vaccine in mice. Virology Journal 10:349 (2013).
Wennier et al., A Novel Naturally Occurring Tandem Promoter in Modified Vaccinia Virus Ankara Drives Very Early Gene Expression and Potent Immune Responses. PLoS ONE 8(8): e73511 (2013).
Wyatt et al., Development of a replication-deficient recombinant vaccinia virus vaccine effective against parainfluenza virus 3 infection in an animal model. Vaccine 14:1451-1458 (1996).
Wyatt et al., Highly attenuated smallpox vaccine protects mice with and without immune deficiencies against pathogenic vaccinia virus challenge. PNAS 2004 101:4590-5. (2004).
Written Opinion and Search Report of the International Search Authority for PCT/EP2015/055239, dated Jul. 9, 2015.

* cited by examiner

USE OF OIL AND WATER EMULSIONS FOR INCREASING B CELL RESPONSES WITH MODIFIED VACCINIA ANKARA VIRUS

This application is a National Phase application under 35 U.S.C. § 371 of International Application No. PCT/EP2015/055239, filed Mar. 12, 2015, and claims the benefit under 35 U.S.C. § 119 (e) U.S. Provisional Patent Application 61/951,672 filed Mar. 12, 2014, the disclosures of which are incorporated by reference herein in their entirety.

BACKGROUND OF THE INVENTION

Vaccines are used to induce specific immune responses against antigens, particularly against pathogen and tumor antigens. Adjuvants can be used to increase the humoral and/or cellular immune response to the antigen. With the aid of adjuvant, a smaller dose of antigen may be required to stimulate the immune response.

Adjuvants can be particulate adjuvants or non-particulate adjuvants. Particulate adjuvants can exist as microparticles in which the immunogen is incorporated into the microparticles. These microparticles may function by a depot mechanism, allowing slower clearance of the antigen from the injection site.

One example of a particulate adjuvant is an oil and water emulsion. For example, Freund's Complete Adjuvant is a water-in-oil emulsion composed of mineral oil mixed with killed Mycobacteria and an emulsifying agent. Incomplete Freund's Adjuvant lacks the mycobacterial components. Mineral oil in an emulsion can be replaced with metabolizable oil. U.S. Pat. Nos. 5,718,904 and 5,690,942.

ADDAVAX is a squalene-based oil-in-water emulsion used with vaccines. ADDAVAX is an adjuvant based on nano-emulsification of 2 components: sorbitan trioleate (0.5% w/v) in squalene oil (5% v/v) and TWEEN 80 (0.5% w/v) in sodium citrate buffer (10 mM, pH 6.5).

MONTANIDE™ ISA51 and ISA720 are adjuvants which allow the manufacture of water-in-oil emulsions. ISA51 is based on mineral oil (50/50 W/O) and ISA720 is based on nonmineral oil (30/70 W/O). They both contain mannide monooleate as an emulsifier.

U.S. Pat. No. 4,650,677 discusses the use of live, attenuated Aujesky virus, Infectious Bovine Rhinotracheitis virus, and Respiratory Syncytial Virus vaccines in oil-in-water emulsions for vaccination. This patent indicates there may be a protective action of the o/w-emulsion on the live virus against neutralization by the antibodies which are present in the animal.

Ganne et al., *Vaccine* 12:1190-1196 (1994) discusses the use of various oil and water emulsions with an adenoviral vector expressing a pseudorabies virus gp50 protein. Although Ganne et al. showed that one of the oil adjuvants combined with the adenovirus could increase anti-gp50 immune responses, the results demonstrated that free gp50 played a significant role in this response.

Kyriakis et al., *Vaccine* 27:2258-2264 (2009) gently mixed a vaccinia vector vaccine, NYVAC, with a solution of 20% adjuvant (oil-in-water emulsion) and 80% PBS prior to administration, and the immunogenicity was improved.

WO 2012/042279 discusses the use of MONTANIDE™ ISA720 in a two or three stage immunization regime in which a protein, an adenoviral vector expressing the protein, and a recombinant MVA vector expressing the protein were administered either separately, or in various combinations. The protein was used with MONTANIDE™ ISA720 adjuvant, including the recombinant MVA in combination with the purified protein with MONTANIDE™ ISA720. Thus, in this regime, the recombinant MVA with adjuvant additionally contained the recombinant protein encoded by the recombinant MVA. WO 2012/042279 did not show any effect of using MONTANIDE™ ISA720 with the recombinant MVA. Douglas et al., *Vaccine* 28:7167-7178 (2010) presented similar results.

Modified Vaccinia virus Ankara (MVA) has been administered to over 100,000 individuals during the smallpox eradication campaign without any complications. However, MVA still represents a complex mixture of viruses with different levels of attenuation and immunogenicity. Suter et al., *Vaccine* 27, 7442-7450 (2009). The plaque-purified MVA developed by Bavarian Nordic (MVA-BN) completely fails to replicate in mammals including humans and is safe even in immune-compromised hosts. Id. Besides its excellent safety profile, MVA is highly immunogenic in humans (Vollmar et al., *Vaccine* 24, 2065-2070 (2006)) and its efficacy has been proven in several smallpox animal models such as Ectromelia virus (ECTV), rabbitpox or monkeypox (Garza et al., *Vaccine* 27, 5496-5504 (2009); Samuelsson et al., *J. Clin. Invest* 118, 1776-1784 (2008); Stittelaar et al., *J. Virol.* 79, 7845-7851 (2005)). Another major advantage of MVA is its capacity to support the genetic insertion of several antigens (Timm et al., *Vaccine* 24, 4618-4621 (2006)) that could concomitantly induce protection against other infectious diseases or cancer ((Harrer et al. *Antivir. Ther.* 10, 285-300 (2005); Mandl et al., *Cancer Immunol. Immunother.* (2011); Meyer et al., *Cancer Immunol. Immunother.* 54, 453-467 (2005)). Vaccinia viruses have a cloning capacity of at least 25,000 bp of foreign DNA (Smith and Moss, *Gene* 25, 21-28 (1983)). Vaccinia virus can accommodate more than 29,000 bp as shown by cloning the cDNA of the complete genome of a feline coronavirus in vaccinia virus (Tekes et al., *J. Virol.* 82, 1851-1859 (2010)).

MVA is used for immunizations, frequently given in a prime and a boosting dose. Thus, a need in the art exists for compositions and methods for vaccination to achieve strong T-cell and/or antibody responses using a single dose and/or a smaller dose. The invention fulfills this need.

BRIEF SUMMARY OF THE INVENTION

The invention encompasses compositions and methods for administration to an animal, especially a human. In one embodiment, the invention encompasses a pharmaceutical composition for inducing an immune response against a vaccinia virus in an animal, particularly a human.

The invention encompasses a composition comprising a recombinant or non-recombinant modified vaccinia Ankara (MVA) virus in an oil and water emulsion. Preferably, the composition comprises a dose of at least $2 \times 10^7$ TCID$_{50}$ of the MVA or recombinant MVA.

Preferably, the composition induces at least a 2-fold, 5-fold, 10-fold or 16-fold higher level of vaccinia neutralizing antibodies at 26 days after immunization when compared to the same composition in the absence of the emulsion.

Preferably, the emulsion is a water-in-oil emulsion or an oil-in-water emulsion. In some embodiments, the emulsion comprises mannide monooleate. In some embodiments, the emulsion comprises a mineral oil, a non-mineral oil, or squalene oil. In some embodiments, the emulsion comprises ISA 51 or ISA720. In some embodiments, the emulsion comprises sorbitan trioleate.

In preferred embodiments, the emulsion does not additionally contain the recombinant protein encoded by the recombinant MVA.

The invention encompasses uses of the compositions of the invention for inducing a neutralizing antibodies against a vaccinia virus in a human.

In invention encompasses compositions for use in the preparation of a medicament and/or vaccine.

In preferred embodiments the invention encompasses compositions for use in the preparation of a medicament and/or vaccine for inducing neutralizing antibodies against a vaccinia virus in a human.

The invention encompasses methods for inducing neutralizing antibodies against a vaccinia virus in a human comprising administering a dose of a composition of the invention to a human.

BRIEF DESCRIPTION OF THE DRAWINGS

FIG. 5 depicts vaccinia-specific T cells responses measured by ELISPOT after immunization with a non-recombinant MVA in an oil and water emulsion.

FIG. 7 depicts serum YFV-specific neutralizing antibody responses measured by PRNT.

FIG. 8 depicts serum RSV-specific neutralizing antibody responses measured by PRNT.

FIG. 19 depicts serum vaccinia-specific neutralizing antibody responses of Example 17 as measured by PRNT after immunization with a dose of $1 \times 10^8$ TCID$_{50}$ MVA-mBN294B, $2 \times 10^7$ TCID$_{50}$, $1 \times 10^7$ TCID$_{50}$, $5 \times 10^6$ TCID$_{50}$ or $1 \times 10^6$ TCID$_{50}$ (RSV) in ISA720.

DETAILED DESCRIPTION OF THE INVENTION

Figure 1:
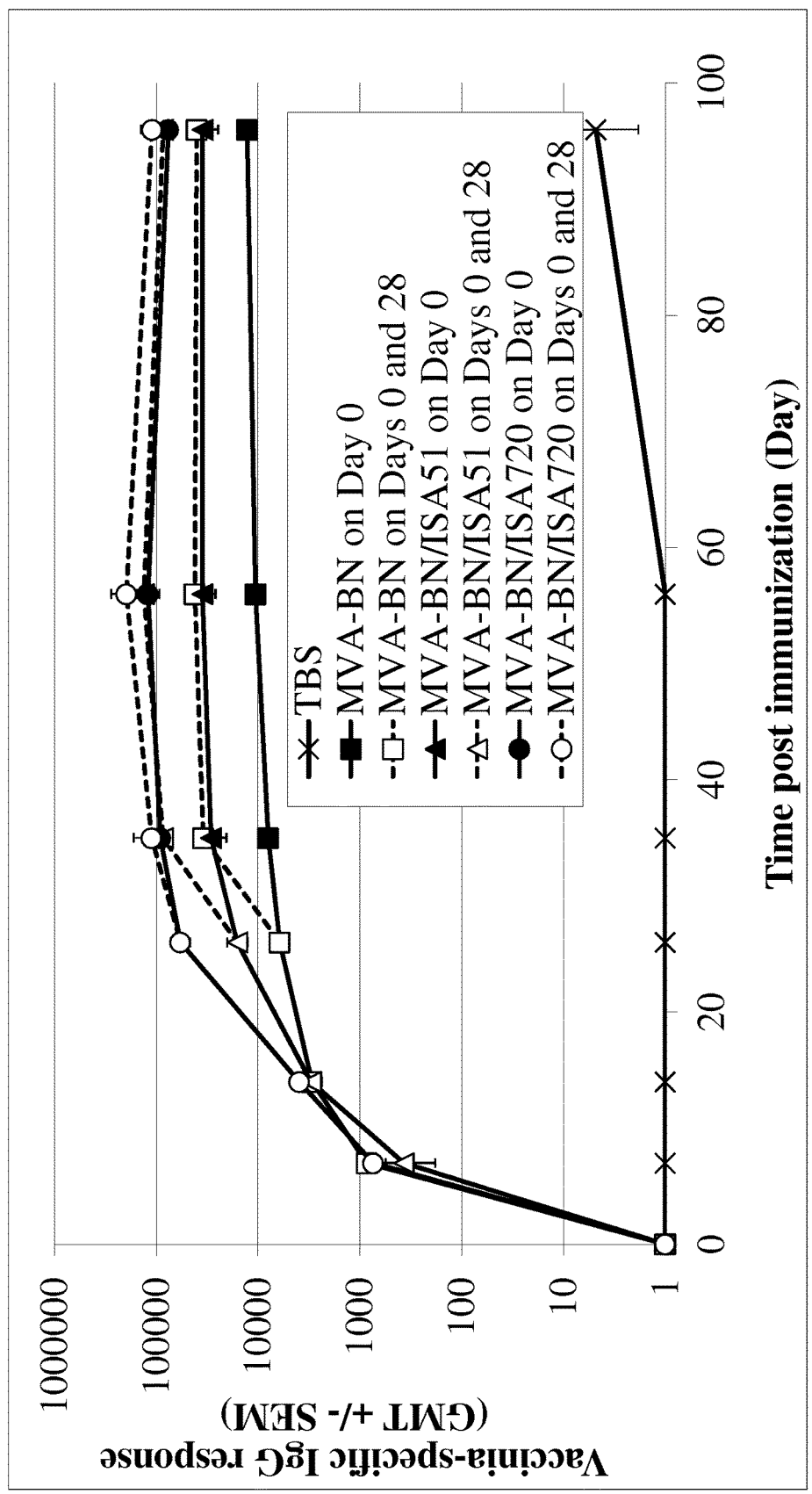
FIG. 1 depicts serum vaccinia-specific IgG responses measured by ELISA after immunization with a dose of $10^8$ non-recombinant MVA in an oil and water emulsion.

As used herein, the term "v/v" designates volume/volume, "w/v" designates weight/volume, and w/w designates weight/weight.

It must be noted that, as used herein, the singular forms "a", "an", and "the", include plural references unless the context clearly indicates otherwise. Thus, for example, reference to "an antigen" includes one or more of antigens and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The term "TCID" is the abbreviation of "tissue culture infectious dose". $TCID_{50}$ is the median tissue culture infective dose; that amount of a pathogenic agent that will produce pathological change in 50% of cell cultures inoculated expressed as $TCID_{50}$/ml. A method for determining $TCID_{50}$ is well known to the person skilled in the art. It is for example described in e.g., Example 2 of WO2003053463.

MVA has been shown to induce strong B cell and T cell response in immunized humans. Here, it is demonstrated that the B cell response induced by MVA can be augmented, particularly the induction of neutralizing antibodies against vaccinia virus or against a heterologous antigen encoded by the MVA.

To investigate the effect of oil and water emulsions on the immune responses induced by MVA, mice were immunized subcutaneously with $1\times10^8$ $TCID_{50}$ of MVA-BN alone or in emulsion with either ISA51 or ISA720 at a ratio of 23:77 (W/O). Unexpectedly, a 5 to 10-fold increase in vaccinia-specific IgG titers was seen with the oil and water emulsions. 26 days after the 1st immunization MVA-BN combined with either ISA51 or ISA720 induced higher vaccinia-specific IgG responses than MVA-BN alone. A single immunization of MVA-BN in ISA51 or ISA720 emulsion induced antibody responses at least equivalent to two immunizations with MVA-BN. A boost effect could further be observed after a second immunization with MVA-BN in ISA51 or ISA720 emulsion.

To determine whether this increase in vaccinia-specific IgG titers was associated with a similar increase in neutralizing antibody titers, the effect of the oil and water emulsions on neutralizing antibody titers was assessed. Unexpectedly, a 2 to 7-fold increase in vaccinia-specific neutralizing antibody titers was seen with the oil and water emulsions. 26 days after the 1st immunization MVA-BN combined with either ISA51 or ISA720 induced higher vaccinia-specific neutralizing antibody responses than MVA-BN alone. A single immunization of MVA-BN in ISA51 or ISA720 emulsion induced at least equivalent vaccinia-specific neutralizing antibody responses than two immunizations with MVA-BN. A boost effect could be observed after a second immunization with MVA-BN in ISA51 or ISA720 emulsion. As neutralizing antibody titers have shown to correlate with protection, an emulsion of MVA-BN in ISA51 or ISA720 is expected to likewise improve protection.

Next, recombinant MVAs were assessed. Mice were immunized subcutaneously with $1\times10^8$ $TCID_{50}$ of a recombinant MVA-BN expressing Yellow Fever Virus (YFV) antigens alone or in emulsion with ISA720 at a W/O ratio of 30/70. Emulsion was either prepared using a single syringe and a needle or with two syringes using an I-connector. Unexpectedly, a greater than 10-fold increase in vaccinia-specific IgG titers was seen with the oil and water emulsions using the recombinant MVA. Thus, a recombinant MVA-BN showed the same effect as a non-recombinant MVA. Emulsions could be prepared either with one syringe and a needle or using an I-connector system.

Next, the effect of various oil and water emulsions was assessed. Mice were immunized subcutaneously with $1\times10^8$ $TCID_{50}$ of a recombinant MVA-BN expressing respiratory syncytial virus (RSV) antigens alone or in emulsion with either ISA720 at two different W/O ratios (30/70 or 50/50) or with ADDAVAX at a 50/50 ratio. In addition one group was treated with $1\times10^8$ $TCID_{50}$ of the recombinant MVA-BN inactivated by UV-treatment. A 5 to 10-fold increase in vaccinia-specific IgG titers was seen with all of the oil and water emulsions using the recombinant MVA. The effect of ISA720 could be observed with different ratios of water:oil (e.g., 23:77; 30:70 or 50:50). In addition, the effect could be obtained with different oil-based adjuvants forming oil and water emulsions (e.g., ISA720, ISA51, ADDAVAX). Moreover, neo-synthesis of proteins by the live attenuated vaccine (after immunization) is required to obtain the optimal effect (UV-treatment).

It was next determined whether the emulsions had any effect on T cell production. Mice were immunized subcutaneously with $1\times10^8$ $TCID_{50}$ of a recombinant MVA-BN expressing YFV antigens alone or in emulsion with ISA720 at a W/O ratio of 30/70 or ADDAVAX at a ratio 50:50. The oil and water emulsions did not significantly impact the T cell response to MVA-BN.

Similarly, mice were immunized subcutaneously with $1\times10^8$ $TCID_{50}$ of a recombinant MVA-BN expressing YFV antigens alone or in emulsion with ISA720 at a W/O ratio of 30/70 or ADDAVAX at a ratio 50:50. Once again, the oil and water emulsions did not significantly impact the T cell response to MVA-BN.

Recombinant antigen-specific neutralizing antibody responses with $1\times10^8$ $TCID_{50}$ recombinant MVA in various oil and water emulsions were assessed. Mice were immunized subcutaneously with $1\times10^8$ $TCID_{50}$ of a recombinant MVA-BN expressing YFV antigens either alone or in emulsion with ISA720 at a W/O ratio of 30/70 or with ADDAVAX at a ratio of 50:50. Unexpectedly, YFV-specific neutralizing antibody titers were increased greater than 10-fold with the oil and water emulsions.

Similarly, mice were immunized subcutaneously with $1\times10^8$ $TCID_{50}$ of a recombinant MVA-BN expressing RSV antigens either alone or in emulsion with ISA720 at different W/O ratios (30/70 or 50/50) or with ADDAVAX at a ratio of 50:50. In addition one group was treated with $1\times10^8$ $TCID_{50}$ of the recombinant MVA-BN expressing RSV antigens inactivated by UV-treatment. Unexpectedly, RSV-specific neutralizing antibody titers were only detected with the oil and water emulsions. Neo-synthesis of proteins by the live attenuated vaccine (after immunization) was required to obtain the optimal effect (UV-treatment).

Next, whether a dose of $1\times10^7$ $TCID_{50}$ MVA could demonstrate these high levels of enhancement of antibody production with oil and water emulsions was investigated. Mice were immunized subcutaneously with $1\times10^7$ $TCID_{50}$ of MVA-BN alone or in emulsion (0.05 ml) with either ISA51 or ISA720 at a ratio of 30:70 (W/O). A small increase in vaccinia-specific IgG titers was seen with the oil and water emulsions.

These mice were further analyzed for vaccinia-specific neutralizing antibody responses by PRNT. No effect on neutralizing antibody titers was seen using $10^7$ $TCID_{50}$ of MVA-BN in an oil and water emulsion.

Figure 18:
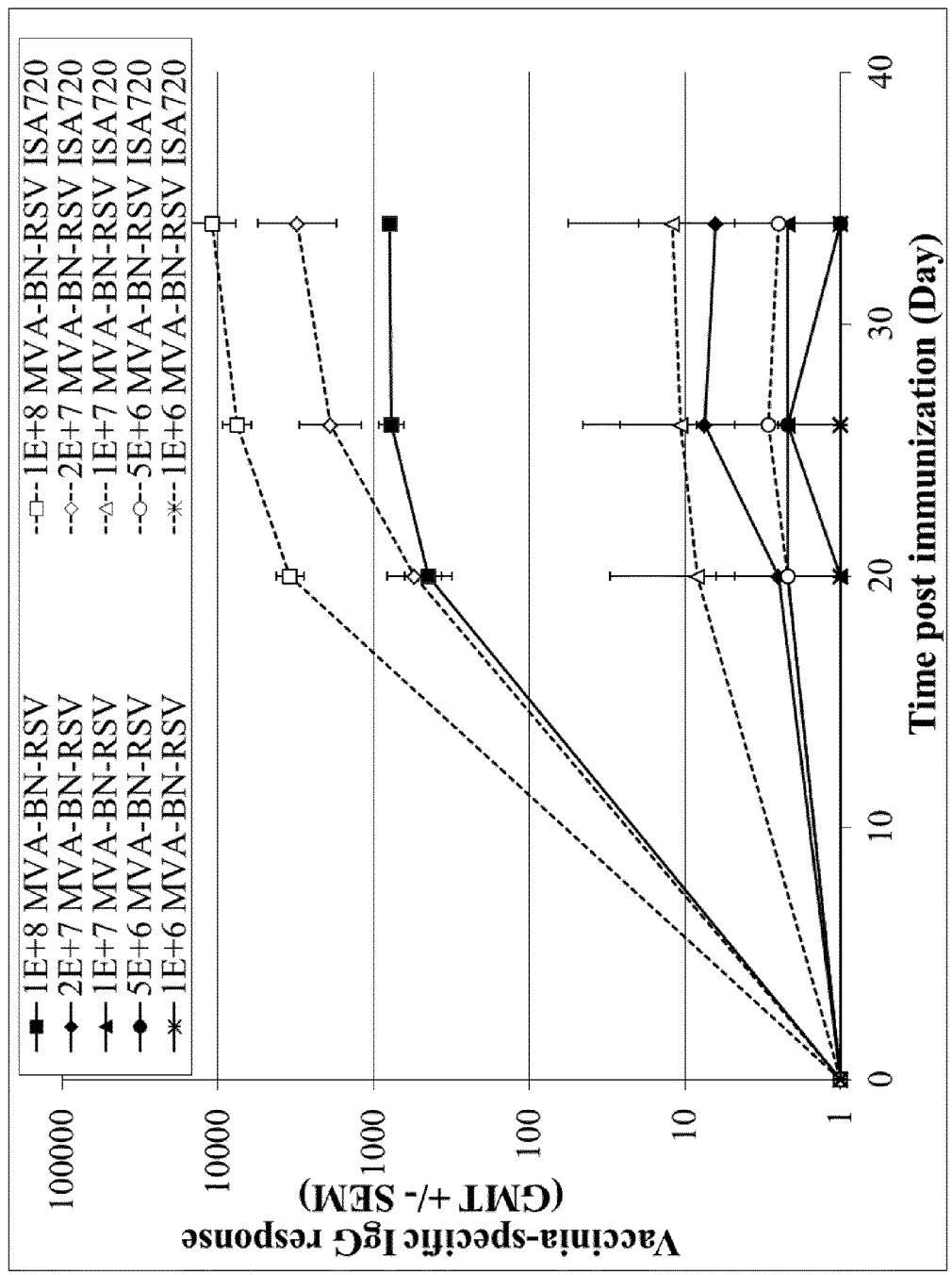
FIG. 18 depicts serum vaccinia-specific IgG responses of Example 17 measured by ELISA after immunization with a dose of $1 \times 10^8$ TCID$_{50}$, $2 \times 10^7$ TCID$_{50}$, $1 \times 10^7$ TCID$_{50}$, $5 \times 10^6$ TCID$_{50}$ or $1 \times 10^6$ TCID$_{50}$ MVA-mBN294B (RSV) and $1 \times 10^8$ TCID$_{50}$, $2 \times 10^7$ TCID$_{50}$, $1 \times 10^7$ TCID$_{50}$, $5 \times 10^6$ TCID$_{50}$ or $1 \times 10^6$ TCID$_{50}$ MVA-mBN2B (RSV) in ISA720 at Days −1, 20, 26 and 34.
Figure 19:
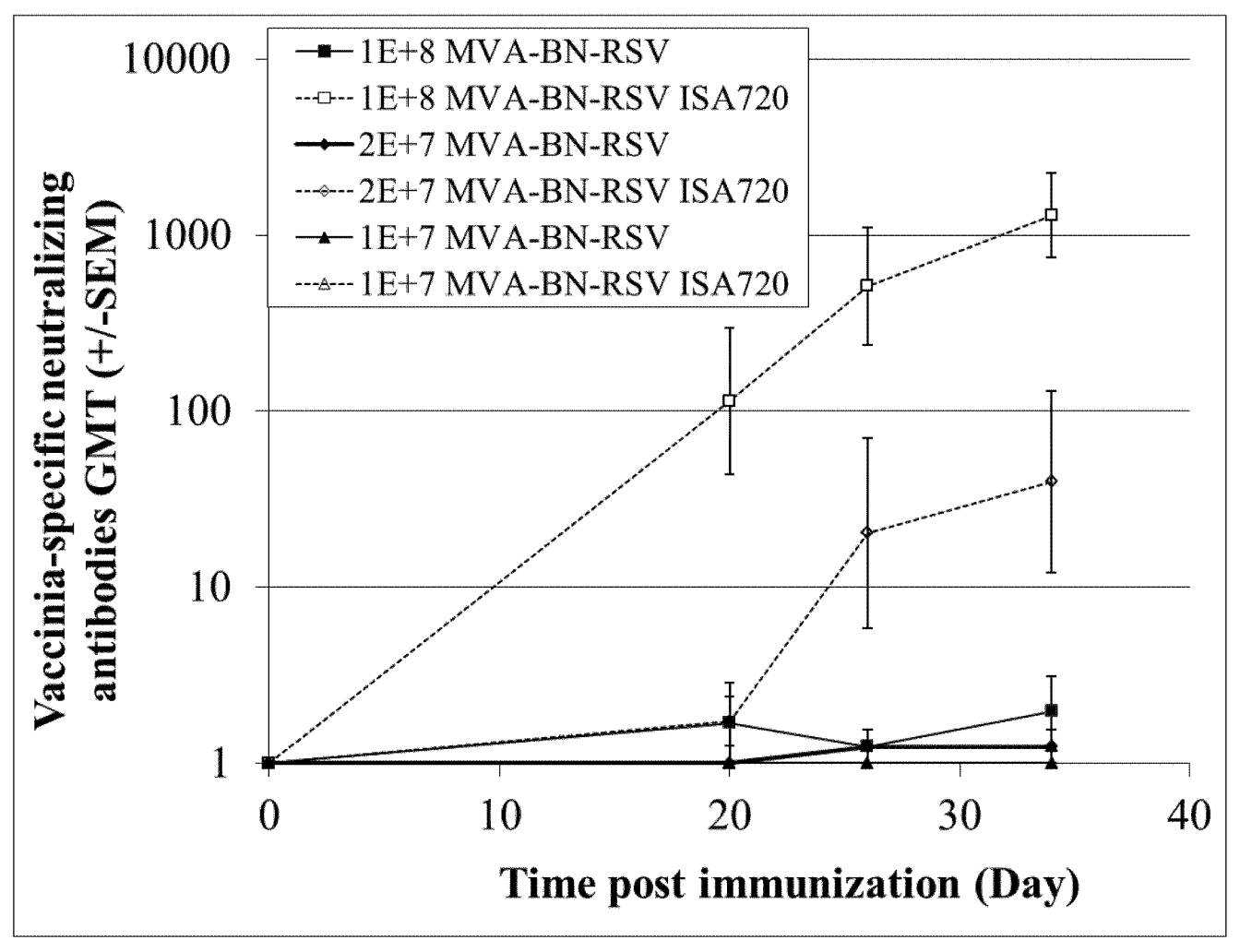

Next, the effect of oil adjuvant on the vaccinia and antigen specific IgG titers and neutralizing antibody response of five different doses of MVA was analyzed according to Example 17. BALB/c mice were immunized subcutaneously (s.c.) with different doses of MVA-BN expressing RSV antigens alone or in emulsion with ISA720 at a W/O ratio of 30/70. Unexpectedly, the oil in water emulsion increased the vaccinia-specific IgG titers by 218 and 492-fold in the $2\times10^7$ TCID$_{50}$ MVA-BN-RSV ISA720 group and 8 to 14-fold in the 1×10$^8$ TCID$_{50}$ MVA-BN-RSV ISA720 group 20 and 35 days after immunization (FIG. 18, Table 1). The effect on the increase in vaccinia-specific neutralizing IgG titers was even more pronounced. A 2 to 32-fold higher vaccinia-neutralizing antibody titer was observed in the 2×10$^7$ TCID$_{50}$ MVA-BN-RSV ISA720 group and a 67 to 656-fold in the 1×10$^8$ TCID$_{50}$ MVA-BN-RSV group 20 and 35 days after immunization (FIG. 19, Table 2). No improvement on antibody response (vaccinia specific as well as neutralizing antibody response) was observed in the groups with less than 2×10$^7$ TCID$_{50}$ MVA-BN-RSV ISA720 compared to those groups without oil (FIG. 19, Table 2).

Next, the effect of oil and water emulsions on recombinant MVA RSV antigen was assessed with 5 recombinant MVA doses between 1×10$^8$ TCID$_{50}$ MVA-BN-RSV and 1×10$^6$ TCID$_{50}$ MVA-BN-RSV. Surprisingly a 8 to 14-fold increase in RSV specific IgG antibodies was seen at 2×10$^7$ TCID$_{50}$ MVA-BN-RSV ISA720 and a 3 to 6-fold increase in RSV specific IgG titers was seen with water in oil emulsions at 1×10$^8$ TCID$_{50}$ MVA-BN-RSV ISA720 compared to the MVA without oil (Table 3).

Also rabbits were immunized i.m. with different dose of MVA-BN-YF with or without ISA720 according to Example 18. Despite less than ⅓ dose of the MVA-BN-YF in Group 3 (1.08×10$^8$ TCID$_{50}$ in 350 µl ISA720) compared to group 4 (MVA-BN-YF alone), this vaccine dose in emulsion with 350 µl ISA720 led to more than a 2-fold increase of the vaccinia-specific antibody response after the first immunization (GMT of 10115 on Day 21), which was almost equivalent to the response obtained after two immunizations with MVA-BN-YF alone. More than a 4-fold increase was obtained after the second immunization (GMT of 81429 on Day 42). Twice the dose of MVA-BN-YF with ISA720 (2.16×10$^8$ TCID$_{50}$ in 700 µl ISA720) in Group 2 led to more than a 3-fold increase of the vaccinia-specific antibody response after the first immunization (GMT of 12734 on Day 21) and more than 8-fold after the second immunization (GMT of 157719 on Day 42) compared to Group 4 (MVA-BN-YF alone). Similar to the vaccination with MVA-BN-YF alone, a third vaccination with MVA-BN-YF in emulsion with ISA720 did not increase the vaccinia-specific antibody

TABLE 1

Vaccinia-specific IgG response at different MVA doses (ELISA)

| | Group 1 1 × 10$^8$ MVA-BN-RSV | | | | Group 2 1 × 10$^8$ MVA-BN-RSV ISA720 | | | | Fold |
|---|---|---|---|---|---|---|---|---|---|
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 447 | 186 | 132 | 100 | 3454 | 781 | 637 | 100 | 8 |
| 26 | 771 | 158 | 131 | 100 | 7576 | 1782 | 1443 | 100 | 10 |
| 34 | 786 | 67 | 61 | 100 | 10873 | 4491 | 3178 | 100 | 14 |
| | Group 3 2 × 10$^7$ MVA-BN-RSV | | | | Group 4 2 × 10$^7$ MVA-BN-RSV ISA720 | | | | Fold |
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 3 | 4 | 2 | 20 | 547 | 272 | 182 | 100 | 218 |
| 26 | 7 | 18 | 5 | 40 | 1897 | 1096 | 695 | 100 | 253 |
| 34 | 6 | 14 | 4 | 40 | 3104 | 2433 | 1364 | 100 | 492 |
| | Group 5 1 × 10$^7$ MVA-BN-RSV | | | | Group 6 1 × 10$^7$ MVA-BN-RSV ISA720 | | | | Fold |
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 1 | 0 | 0 | 0 | 8 | 22 | 6 | 40 | 8 |
| 26 | 2 | 3 | 1 | 20 | 11 | 35 | 8 | 40 | 5 |
| 34 | 2 | 3 | 1 | 20 | 12 | 44 | 9 | 40 | 6 |
| | Group 7 5 × 10$^6$ MVA-BN-RSV | | | | Group 8 5 × 10$^6$ MVA-BN-RSV ISA720 | | | | Fold |
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 2 | 3 | 1 | 20 | 2 | 3 | 1 | 20 | 1 |
| 26 | 2 | 3 | 1 | 20 | 3 | 5 | 2 | 20 | 1 |
| 34 | 1 | 0 | 0 | 0 | 3 | 4 | 2 | 20 | 3 |

TABLE 1-continued

Vaccinia-specific IgG response at different MVA doses (ELISA)

| | Group 9 $1 \times 10^6$ MVA-BN-RSV | | | | Group 10 $1 \times 10^6$ MVA-BN-RSV ISA720 | | | | Fold |
|---|---|---|---|---|---|---|---|---|---|
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 1 | 0 | 0 | 0 | 1 | 0 | 0 | 0 | 1 |
| 26 | 1 | 0 | 0 | 0 | 1 | 0 | 0 | 0 | 1 |
| 34 | 1 | 0 | 0 | 0 | 1 | 0 | 0 | 0 | 1 |

Geometric mean titer (GMT), standard error of the mean SEM, positive and negative graphic representation of the SEM on an antilogarithmic scale (Plot+ and −), % sero-conversion rate

TABLE 2

Vaccinia-specific neutralizing IgG response (PRNT)

| | Group 1 $1 \times 10^8$ MVA-BN-RSV | | | | Group 2 $1 \times 10^8$ MVA-BN-RSV ISA720 | | | | Fold |
|---|---|---|---|---|---|---|---|---|---|
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 2 | 1 | 1 | 20 | 114 | 183 | 70 | 100 | 67 |
| 26 | 1 | 0 | 0 | 20 | 514 | 595 | 276 | 100 | 413 |
| 34 | 2 | 1 | 1 | 40 | 1295 | 955 | 550 | 100 | 656 |

| | Group 3 $2 \times 10^7$ MVA-BN-RSV | | | | Group 4 $2 \times 10^7$ MVA-BN-RSV ISA720 | | | | Fold |
|---|---|---|---|---|---|---|---|---|---|
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 1 | 0 | 0 | 0 | 2 | 1 | 0 | 50 | 2 |
| 26 | 1 | 0 | 0 | 20 | 20 | 50 | 14 | 80 | 16 |
| 34 | 1 | 0 | 0 | 20 | 40 | 90 | 28 | 100 | 32 |

Geometric mean titer (GMT), standard error of the mean SEM, positive and negative graphic representation of the SEM on an antilogarithmic scale (Plot+ and −), % sero-conversion rate

TABLE 3

RSV-specific IgG response (ELISA)

| | Group 1 $1 \times 10^8$ MVA-BN-RSV | | | | Group 2 $1 \times 10^8$ MVA-BN-RSV ISA720 | | | | Fold |
|---|---|---|---|---|---|---|---|---|---|
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 433 | 237 | 153 | 100 | 1388 | 291 | 241 | 100 | 3 |
| 26 | 335 | 78 | 63 | 100 | 2013 | 169 | 156 | 100 | 6 |
| 34 | 940 | 479 | 317 | 100 | 2392 | 194 | 179 | 100 | 3 |

| | Group 3 $2 \times 10^7$ MVA-BN-RSV | | | | Group 4 $2 \times 10^7$ MVA-BN-RSV ISA720 | | | | Fold |
|---|---|---|---|---|---|---|---|---|---|
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 69 | 217 | 52 | 75 | 558 | 164 | 127 | 100 | 8 |
| 26 | 207 | 100 | 67 | 100 | 1308 | 175 | 154 | 100 | 6 |
| 34 | 119 | 286 | 84 | 80 | 1705 | 427 | 341 | 100 | 14 |

TABLE 3-continued

RSV-specific IgG response (ELISA)

| | Group 5 $1 \times 10^7$ MVA-BN-RSV | | | | Group 6 $1 \times 10^7$ MVA-BN-RSV ISA720 | | | | Fold |
|---|---|---|---|---|---|---|---|---|---|
| Day | GMT | Plot+ | Plot− | % | GMT | Plot+ | Plot− | % | increase |
| 0 | 1 | 0 | 0 | 0 | 1 | 0 | 0 | 0 | 1 |
| 20 | 12 | 21 | 8 | 60 | 12 | 42 | 9 | 40 | 1 |
| 26 | 88 | 4 | 4 | 100 | 11 | 107 | 10 | 33 | 0 |
| 34 | 54 | 96 | 34 | 80 | 18 | 88 | 15 | 40 | 0 |

Geometric mean titer (GMT), standard error of the mean SEM, positive and negative graphic representation of the SEM on an antilogarithmic scale (Plot+ and −), % sero-conversion rate response any further, independent of the dose used. So surprisingly using ISA720 adjuvant, 2- or 3-fold higher responses were obtained after the first administration and 4- and 8-fold higher responses after the boost, despite the ⅓ or ⅔ reductions of the MVA-BN-YF dose, respectively. This response was almost equivalent to the response induced by two vaccinations with MVA-BN-YF without adjuvant.

Based on these results, it is apparent that the addition of an oil and water emulsion to MVA can vastly increase the B cell response and particularly neutralizing antibodies against vaccinia virus and encoded recombinant antigens. A wide variety of emulsions can be used to produce this effect. The effect on neutralizing antibodies was not seen using $10^7$ $TCID_{50}$.

The invention encompasses compositions, uses, and methods for inducing a B cell response, particularly neutralizing antibodies. In one embodiment, the invention encompasses administering a dose of at least $2 \times 10^7$ $TCID_{50}$ of an MVA in an oil and water emulsion to a human.

Modified Vaccinia Ankara (MVA) Viruses

The invention encompasses any and all MVA viruses. Preferred MVA viruses include MVA variant strains such as MVA-BN (deposited at the European Collection of Animal Cell Cultures, Vaccine Research and Production Laboratory, Public Health Laboratory Service, Centre for Applied Microbiology and Research, Porton Down, Salisbury, Wiltshire SP4 0JG, United Kingdom (ECACC) on Aug. 30, 2000, under Accession No. V00083008), MVA-575 (deposited at ECACC on Dec. 7, 2000, under Accession No. V00120707), and MVA-572 (deposited at ECACC on Jan. 27, 1994 under Accession No. V94012707). Derivatives of the deposited strain are also preferred.

Preferably, the MVA has the capability of reproductive replication in vitro in chicken embryo fibroblasts (CEF) or other avian cell lines or in vivo in embryonated eggs, but no capability of reproductive replication in human cells in which MVA 575 or MVA 572 can reproductively replicate.

Most preferably, the MVA has no capability of reproductive replication in the human keratinocyte cell line HaCaT, the human embryo kidney cell line 293 (also referred to as HEK293), the human bone osteosarcoma cell line 143B, and the human cervix adenocarcinoma cell line HeLa.

In preferred embodiments, the Modified vaccinia virus Ankara (MVA) virus is characterized by having the capability of reproductive replication in vitro in chicken embryo fibroblasts (CEF) and by being more attenuated than MVA-575 in the human keratinocyte cell line HaCaT, in the human bone osteosarcoma cell line 143B, and in the human cervix adenocarcinoma cell line HeLa. Preferably, the MVA virus is capable of an amplification ratio of greater than 500 in CEF cells. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

Recombinant MVAs

The invention encompasses recombinant MVA viruses generated with any and all MVA viruses. In one embodiment, the recombinant MVA virus is a recombinant MVA-BN virus. The recombinant MVA virus comprises at least one heterologous nucleic acid sequence. In the context of this invention, the term "heterologous" nucleic acid sequence refers to a nucleic acid sequence that is not naturally found in the MVA.

Preferably, the heterologous nucleic acid sequence is a sequence coding for at least one antigen, antigenic epitope, and/or a therapeutic compound. The antigenic epitopes and/or the antigens can be antigenic epitopes and/or antigens of an infectious agent. The infectious agents can be viruses, fungi, pathogenic unicellular eukaryotic or prokaryotic organisms, and parasitic organisms. In some embodiments, the infectious agent is a virus selected from any of the following: Norovirus, Rotavirus, Rubella virus, Poliovirus, Influenza virus, Flavivirus (particularly Dengue virus and Yellow Fever virus), Paramyxovirus (particularly measles virus, mumps virus, and respiratory syncytial virus (RSV)), Hepatitis virus (particularly Hepatitis A, B, and C viruses), Human immunodeficiency virus (particularly HIV-1), Filovirus (particularly Ebola virus and Marburg virus) or from other viruses causing hemorrhagic fever. In some embodiments, the infectious agent is a bacterium selected from any of the following: *Bacillus anthracis, meningococcus, pneumococcus, Haemophilus influenza, Corynebacterium diphtheriae, Clostridium tetani, Burkholderia, Francisella tularensis, Coxiella burnetii*, or *Bordetella pertussis*.

Any antigen, including those that induce a T-cell response, can be expressed by the recombinant MVA of the invention. Viral, bacterial, fungal, and cancer antigens are preferred. Preferred antigens are antigens of any of the viruses or bacteria described above. HIV-1 antigens, Dengue virus antigens, anthrax antigens, measles virus antigens, influenza virus antigens, picornavirus antigens, norovirus antigens, coronavirus antigens and respiratory syncytial virus antigens are particularly preferred antigens. Preferably, the antigen is a foreign antigen or neoantigen. Within the context of this invention, the term "neoantigen" refers to an antigen not naturally expressed by the poxviral vector.

In some embodiments, the administration induces T- and/or B-cell responses against a heterologous antigen encoded by the recombinant MVA. The T-cell response can be an effector and/or long term memory T-cell response. The B-cell response can be a neutralizing antibody response.

The invention also encompasses non-recombinant MVA viruses. The non-recombinant MVA virus does not comprise any heterologous nucleic acid sequence.

The invention encompasses recombinant MVAs comprising one or more heterologous nucleic acid sequence incorporated in a variety of insertion sites in the MVA genome.

The invention also encompasses an MVA that does not comprise any neoantigen.

In one embodiment, the heterologous nucleic acid sequence(s) is/are inserted into an intergenic region (IGR) of the MVA. In preferred embodiments, the IGR is selected from IGR07/08, IGR 44/45, IGR 64/65, IGR 88/89, IGR 136/137, and IGR 148/149. Preferably, less than 5, 4, 3, or 2 IGRs of the recombinant MVA comprise the heterologous nucleic acid sequence(s). In a particularly preferred embodiment, the recombinant MVA comprises 1, 2, 3, 4, 5, 6, 7, 8, or more heterologous nucleic acid sequence(s) inserted into 1, 2, 3, or 4 IGR(s).

In one embodiment, the heterologous nucleic acid sequence(s) is/are inserted into naturally occurring deletion sites I, II, III, IV, V, or VI of the MVA.

The number of insertion sites of MVA comprising heterologous nucleic acid sequences can be 1, 2, 3, 4, 5, 6, 7, or more. In preferred embodiments, the recombinant MVA comprises heterologous nucleic acid sequences inserted into 4, 3, 2, or less insertion sites. Most preferably, 1 or 2 insertion sites are used.

The recombinant MVA virus can be generated by routine methods known in the art. For example, the MVA virus can be generated by following the procedures set out in the Examples.

Methods to obtain recombinant poxvirus vectors or to insert exogenous coding sequences into a poxviral genome are well known to the person skilled in the art. For example, methods are described in the following references: Molecular Cloning, A laboratory Manual. Second Edition. By J. Sambrook, E. F. Fritsch and T. Maniatis. Cold Spring Harbor Laboratory Press. 1989: describes techniques for standard molecular biology techniques such as cloning of DNA, DNA and RNA isolation, western blot analysis, RT-PCR and PCR amplification techniques. Virology Methods Manual. Edited by Brian W J Mahy and Hillar O Kangro. Academic Press. 1996: describes techniques for the handling and manipulation of viruses. Molecular Virology: A Practical Approach. Edited by A J Davison and R M Elliott. The Practical Approach Series. IRL Press at Oxford University Press. Oxford 1993. Chapter 9: Expression of genes by Vaccinia virus vectors. Current Protocols in Molecular Biology. Publisher: John Wiley and Son Inc. 1998. Chapter 16, section IV: Expression of proteins in mammalian cells using vaccinia viral vector describes techniques and know-how for the handling, manipulation and genetic engineering of MVA.

For the generation of recombinant poxviruses according to the present invention, different methods may be applicable. The heterologous nucleic acid sequence to be inserted into the virus can be placed into an *E. coli* plasmid construct into which DNA homologous to a section of DNA of the poxvirus has been inserted. Separately, the heterologous nucleic acid sequence can be ligated to a promoter. The promoter-gene linkage can be positioned in the plasmid construct so that the promoter-gene linkage is flanked on both ends by DNA homologous to a DNA sequence flanking a region of poxviral DNA containing a non-essential locus. The resulting plasmid construct can be amplified by propagation within *E. coli* bacteria and isolated. The isolated plasmid containing the heterologous nucleic acid sequence can be transfected into a cell culture, e.g., chicken embryo fibroblasts (CEFs), along with infection of this culture by the poxvirus. Recombination between homologous poxviral DNA in the plasmid and the viral genome, respectively, can generate a poxvirus modified by the presence of the heterologous nucleic acid sequence.

According to a preferred embodiment, a cell of a suitable cell culture as, e.g., CEF cells, can be infected with a poxvirus. The infected cell can be, subsequently, transfected with a first plasmid vector comprising a foreign gene or genes, preferably under the transcriptional control of a poxvirus expression control element. As explained above, the plasmid vector also comprises sequences capable of directing the insertion of the heterologous nucleic acid sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase, xanthine-guanine phosphoribosyl transferase gene, or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second heterologous nucleic acid sequence or sequences. In case, this heterologous nucleic acid sequence can be introduced into a different insertion site of the poxviral genome, the second vector also differs in the poxvirus-homologous sequences directing the integration of the second heterologous nucleic acid sequence or sequences into the genome of the poxvirus. After homologous recombination has occurred, the recombinant virus comprising two or more heterologous nucleic acid sequences can be isolated. For introducing additional heterologous nucleic acid sequences into the recombinant virus, the steps of infection and transfection can be repeated by using the recombinant virus isolated in previous steps for infection and by using a further vector comprising a further heterologous nucleic acid sequence or sequences for transfection.

Alternatively, the steps of infection and transfection as described above are interchangeable, i.e., a suitable cell can at first be transfected by the plasmid vector comprising the heterologous nucleic acid sequence or sequences and, then, infected with the poxvirus. As a further alternative, it is also possible to introduce each heterologous nucleic acid sequence into different viruses, coinfect a cell with all the obtained recombinant viruses and screen for a recombinant including all heterologous nucleic acid sequences. A third alternative is ligation of DNA genome and heterologous nucleic acid sequence or sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

In one embodiment, expression of one, more, or all of the heterologous nucleic acid sequences is under the control of one or more poxvirus promoters. In preferred embodiments, the poxvirus promoter is a Pr7.5 promoter, a hybrid early/late promoter, a PrS promoter, a synthetic or natural early or late promoter, or cowpox virus ATI promoter.

A heterologous nucleic acid sequences(s) can be expressed as a single transcriptional unit. For example, heterologous nucleic acid sequences(s) can be operably linked to a vaccinia virus promoter and/or linked to a vaccinia virus transcriptional terminator. In one embodiment, one or more heterologous nucleic acid sequences(s) are expressed as a fusion protein.

The "transcriptional unit" can be inserted by itself into an insertion site in the MVA genome. The "transcriptional unit" can be inserted with other transcriptional unit(s) into an insertion site in the MVA genome. The "transcriptional unit" is not naturally occurring (i.e., heterologous or exogenous or foreign) in the MVA genome and is capable of transcription in infected cells.

Preferably, the recombinant MVA comprises 1, 2, 3, 4, 5, 6, 7, 8, 9, 10, or more heterologous nucleic acid sequences(s) inserted into the MVA genome. In one embodiment, the recombinant MVA stably expresses heterologous nucleic acid sequences(s) encoded by 1, 2, 3, 4, 5, 6, 7, 8, 9, 10, or more transcriptional units.

In various embodiments, recombinant MVA comprises 3, 4, 5, 6, 7, 8, 9, 10, or more transcriptional units inserted into the MVA genome at 1, 2, 3, 4, 5, 6, or more insertion sites in the MVA genome.

The invention encompasses recombinant MVA comprising one or more of SEQ ID NOs: 1-6, particularly those combinations set forth in the examples. The invention further encompasses the recombinant MVAs set forth in the in the examples and modifications thereof.

Pharmaceutical Compositions

The invention encompasses pharmaceutical compositions and vaccines comprising at least $10^6$, $10^7$, or $10^8$ TCID$_{50}$ of an MVA for administration to animal, especially human. Preferably, the composition comprises at least $10^6$ TCID$_{50}$, $2\times10^6$ TCID$_{50}$, $3\times10^6$ TCID$_{50}$, $4\times10^6$ TCID$_{50}$, $5\times10^6$ TCID$_{50}$, $6\times10^6$ TCID$_{50}$, $7\times10^6$ TCID$_{50}$, $8\times10^6$ TCID$_{50}$, $9\times10^6$ TCID$_{50}$, $10^7$ TCID$_{50}$, $2\times10^7$ TCID$_{50}$, $3\times10^7$ TCID$_{50}$, $4\times10^7$ TCID$_{50}$, $5\times10^7$ TCID$_{50}$, $6\times10^7$ TCID$_{50}$, $7\times10^7$ TCID$_{50}$, $8\times10^7$ TCID$_{50}$, $9\times10^7$ TCID$_{50}$, $10^8$ TCID$_{50}$, $2\times10^8$ TCID$_{50}$, $3\times10^8$ TCID$_{50}$, $4\times10^8$ TCID$_{50}$, $5\times10^8$ TCID$_{50}$, $6\times10^8$ TCID$_{50}$, $7\times10^8$ TCID$_{50}$, $8\times10^8$ TCID$_{50}$, $9\times10^8$ TCID$_{50}$, or $10^9$ TCID$_{50}$ of an MVA. A particularly preferred dose is at least $5\times10^7$ TCID$_{50}$, $6\times10^7$ TCID$_{50}$, $7\times10^7$ TCID$_{50}$, $8\times10^7$ TCID$_{50}$, $9\times10^7$ TCID$_{50}$, or $10^8$ TCID$_{50}$ of an MVA. Preferred is a dose of at least $2\times10^7$ TCID$_{50}$, more preferably a dose of at least $5\times10^7$ TCID$_{50}$. Especially preferred is a dose of $10^8$ TCID$_{50}$. In another preferred embodiment the dose is between equal to or above $2\times10^7$ TCID$_{50}$ to $5\times10^8$ TCID$_{50}$, preferably between equal to or above $2\times10^7$ TCID$_{50}$ to $1.5\times10^8$ TCID$_{50}$.

Preferably, the pharmaceutical composition is in a volume of at least 35 μl, 70 μl, 100 μl, 150 μl, 200 μl, 250 μl, 300 μl, 350 μl, 400 μl, 500 μl, 600 μl, 750 μl, 800 μl or 1000 μl, preferably in a volume between 35 μl to 600 μl, between 100 μl to 600 μl, between 450 μl to 800 μl, between 250 μl to 600 μl, between 250 μl to about 1000 μl or 250 μl to about 500 μl.

The term "animal" means any organism belonging to the kingdom Animalia and includes humans.

Oil and Water Emulsions

The invention encompasses oil-in-water (O/W), water-in-oil (W/O), and water-in-oil-in-water (W/O/W) emulsions.

The term "oil-in-water emulsion" means an emulsion in which small droplets of oil are suspended in a continuous water phase. Usually, an oil-emulsion is composed of an aqueous phase, which can be made up of water, saline or a buffer (e.g., Phosphate Buffered Saline), an oil phase and one or more emulsifiers, which components are extensively mixed by known techniques until a stable emulsion is obtained. The type of emulsion which the emulsifier is likely to promote is indicated by its relative affinity for oil and water, which is known as its hydrophilic-lipophilic balance (HLB). Generally, emulsifiers with an HLB of about 3-6 are required for the production of w/o-type emulsions. Suitable emulsifiers for o/w-type emulsions are usually found in the range of 10-18 (HLB). It is also general practice to combine two or more emulsifiers in such a way that a desired HLB value is obtained. Details concerning the production of pharmaceutical oil-emulsions can be found, for example, in: "The Theory and Practice of Industrial Pharmacy" (eds.: Lachman, L. et al., Lea & Febiger, Philadelphia, U.S.A., 1970, Chapter 16), "Remington's Pharmaceutical Sciences" (ed.: Gennaro, A. R., Mack Publishing Company, Easton, U.S.A., 1990, 18th edition, "Bio-emulsifiers", Zajic, J. E. et al. (in CRC Critical Reviews in microbiology, 1976, 19-66).

Preferably, the emulsion contains about 20 to 75% v/v of the vaccine formulation of the invention, more preferably about 25 to 75% of the vaccine, and even more desirably about 45 to 75% thereof. Amounts of 48 to 73% or 65 to 75% may be even more preferred.

The emulsions preferably contain an oil selected from mineral oil, non-mineral oil, squalene, vegetable oil, nut oil, or animal oil. Preferably, the oil is present at an O/W ratio of about 50:50, 40:60, 30:70, 20:80, or 10:90 for oil-in-water emulsions. Preferably, the oil is present at a W/O ratio of about 50:50, 40:60, 30:70, 20:80, or 10:90 for water-in-oil emulsions. Preferably, the emulsion contains more than 20%, 25%, 30%, 40%, 50%, 60%, 70%, 75%, or 80% oil. Preferably, the emulsion contains about 20 to 75% v/v of the oil adjuvant, more preferably about 25 to 75% v/v oil adjuvant, and even more desirably about 45 to 75% v/v thereof. Amounts of 48 to 73% v/v or 65 to 75% v/v may be even more preferred.

The emulsion preferably contains one or more emulsifier. Emulsifiers are well-known in the art and include mannide oleate, lecithin, TWEEN™ 80 (polyoxyethylene sorbitan monooleate), SPAN™ 20 (sorbitan monolaurate), 80 (sorbitan monooleate), 83 (sorbitan sesquioleate) and 85 (sorbitan trioleate) emulsifiers. In one embodiment, the emulsifier is used at a ratio of 1:10 (v/v) with respect to the oil in an emulsion.

In another embodiment the emulsion can be a MONTANIDE™ Seppic Adjuvant (Montantide ISA) such as ISA51, ISA50, ISA70, ISA206, ISA708, ISA720, ISA763A, ISA207, ISA264, ISA27, ISA35, ISA740, ISA773, ISA266, ISA267, ISA28, or MF59 (Novartis).

In a further embodiment, the emulsion is a metabolizable, non-mineral oil based adjuvant, such as ISA708, ISA720, ISA 763A, ISA207, ISA264, ISA27 and ISA35.

Preferred emulsions contain ISA51 (Seppic), ISA720 (Seppic), and ADDAVAX (InvivoGen). Preferably, ISA51 is used at a w/o ratio of 50:50. Preferably, ISA720 is used at a w/o ratio of 50:50, 30:70 or 23:77. Preferably, ADDAVAX is used at a ratio of 1:1 (v/v) with the MVA in aqueous solution.

Preferably, the emulsion is in a volume of at least 35 µl, 70 µl, 100 µl, 150 µl, 200 µl, 250 µl, 300 µl, 350 µl, 400 µl, or 500 µl.

More preferably, the emulsion of any embodiment of the invention is used in a ratio between 1:5 to 1:3 aqueous MVA virus:oil and water emulsion, preferably in a ratio between 1:4 to 1.3, preferably wherein the oil and water emulsion is ISA720.

Administration

An animal, especially a human, can be vaccinated with a single administration of the MVA in an oil and water emulsion in the absence of any additional ("boosting") administrations. In other embodiments, one or more boosting administrations are administered. In one embodiment, a second administration is given four weeks to eight weeks after the first vaccination administration. Preferably, the second administration is given at 2, 4, 6, or 8 weeks after the first administration. In other embodiments, a third, fourth, fifth, sixth, seventh, eighth, ninth, tenth, or additional administration is given.

The boosting administration can be administered to increase the B cell response when the initial response decays or to further increase the initial response. Thus, in some embodiments a boosting administration is provided to augment or reestablish a desired level of immune response.

The time between the first and second administrations and between an administration and a subsequent administration can vary. In one embodiment, the time between administrations is two to six weeks. In various embodiments, the time between administrations is at least 2, 4, 6, 8, 10, 12, 15, 30, or 52 weeks. In various embodiments, the time between administrations is at least 1, 3, 6, 9, 12, 24, 36, or 48 months. In various embodiments, the time between administrations is at least 1, 2, 3, 4, 5, 6, 7, 8, 9, or 10 years.

The invention encompasses administration of a dose of an MVA in an emulsion to an animal, especially human, via any route. Preferred routes of administration include subcutaneous (s.c.), intradermal (i.d.), intramuscular (i.m.), in bone marrow (i.bm.) or intravenous (i.v.) injection, oral administration and mucosal administration, especially intranasal administration, or inhalation. The quantity to be administered (dosage) depends on the subject to be treated, considering among other things the condition of the patient, the state of the individual's immune system, the route of administration and the size of the host. Most preferably, the administration is subcutaneous.

Preferably, the administration is given in a volume of at least 0.05 ml, 0.1 ml, 0.2 ml, 0.3 ml, 0.4 ml, 0.5 ml, 0.6 ml, 0.7 ml, 0.8 ml, 0.9 ml, or 1.0 ml. Most preferably, the administration is given in a volume of at least 35 μl, 70 μl, 100 μl, 150 μl, 200 μl, 250 μl, 300 μl, 350 μl, 400 μl, 500 μl, 600 μl, 750 μl, 800 μl or 1000 μl, preferably in a volume between 35 μl to 600 μl, between 100 μl to 600 μl, between 450 μl to 800 μl, between 250 μl to 600 μl, between 250 μl to about 1000 μl or 250 μl to about 500 μl.

The invention further encompasses MVAs for use as a pharmaceutical composition or vaccine for vaccinating a human, the use of MVAs as pharmaceutical compositions or vaccines for treating a human, and the use of MVAs in the preparation of pharmaceutical compositions or vaccines or medicaments for treating or vaccinating a human.

Additionally or alternatively, provided herein is a MVA, the recombinant MVA, the composition or pharmaceutical composition of any of the embodiments for use in the preparation of a medicament and/or vaccine.

Also provided herein, is the MVA, the recombinant MVA, the composition or pharmaceutical composition of any of the embodiments for use in the preparation of a medicament and/or vaccine, wherein the medicament or vaccine is administered in any of the doses described herein.

Further provided is the MVA, the recombinant MVA, the composition or pharmaceutical composition of any of the embodiments of the invention for use in the preparation of a medicament and/or vaccine for inducing neutralizing antibodies against a modified vaccinia Ankara (MVA) virus in a human.

The pharmaceutical composition, vaccine or medicament can generally include one or more auxiliary substances, such as pharmaceutically acceptable and/or approved carriers, additives, antibiotics, preservatives, adjuvants, diluents and/or stabilizers. Such auxiliary substances can be water, saline, glycerol, ethanol, oil, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of pharmaceutical compositions or vaccines or medicaments, the MVA according to the invention can be converted into a physiologically acceptable form. This can be done based on experience in the preparation of poxvirus vaccines used for vaccination against smallpox (as described by Stickl et al. Prev. Med. 3:97-101 (1974)). The purified virus can be stored at −20° C., or −80° C., frozen in a liquid. Preferably, the virus has a titer of $5\times10^8$ $TCID_{50}$/ml, and can be formulated in a buffered solution, for example, in 10 mM Tris, 140 mM NaCl, at pH 7.4.

The virus formulation can contain additional additives such as mannitol, dextran, sugar, glycine, lactose or polyvinylpyrrolidone or other auxiliary substances, such as antioxidants or inert gas, stabilizers or recombinant proteins (e.g., human serum albumin, or HSA) suitable for in vivo administration.

Alternatively, the vaccine can be produced by stepwise freeze-drying of the virus in a formulation. For example, $10^8$ particles of the virus can be lyophilized in 100 µl to 1 ml of phosphate-buffered saline (PBS) in the presence of 2% peptone and 1% HSA in an ampoule, preferably a glass ampoule. The glass ampoule is then sealed and can be stored between 4° C. and room temperature for several months. However, as long as no need exists the ampoule is stored preferably at temperatures below −20° C.

Immune Response

The invention encompasses the induction of an immune response against a vaccinia virus by administration of a dose of an MVA to a human. Preferably the administration induces protective T- and B-cell responses against the vaccinia virus in the human. Most preferably, the immune response is induced in the absence of a second administration of the MVA. Within the context of this invention, the phrase "the immune response is induced in the absence of a second administration of the MVA" means that the immune response does not depend on the administration of a second (i.e., boosting) dose of the MVA. The immune response is induced by the first administration. Thus, within the context of this invention, the phrase "the immune response is induced in the absence of a second administration of the MVA" does not mean that a second administration is not administered; it only means that a second administration is not required to induce the protective immune response. In some embodiments, a second or subsequent administration is administered. The second or subsequent administration can increase the level of the immune response and/or the longevity of the immune response.

The protective immune response can protect at least 75%, 80%, 90%, 95%, 96%, 97%, 98%, 99% or 100% of the humans to which the MVA is administered from death and/or disease symptoms.

Preferably, the protective immune response is against a variola virus. Most preferably, the protective immune response is against smallpox.

Preferably, the immune response is induced in the within 12, 11, 10, 9, 8, 7, 6, 5, 4, 3, or 2 weeks of the administration.

In one embodiment, the composition induces at least a 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold higher level of vaccinia neutralizing antibodies at 26, 34, 35, 42, 56, 69, 84, or 96 days after immunization when compared to the same composition in the absence of the emulsion.

In one embodiment, the composition induces at least a 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold higher level of vaccinia specific antibodies at 26, 34, 35, 42, 56, 69, 84, or 96 days after immunization when compared to the same composition in the absence of the emulsion.

Whether a composition induces at least an x-fold higher level of vaccinia neutralizing antibodies or vaccinia specific antibodies at y days after immunization when compared to the same composition in the absence of the emulsion can be determined using the assays presented in the Examples, or other comparable assays.

Certain embodiments of the present invention also include the following items:

1. A pharmaceutical composition for inducing vaccinia neutralizing antibodies in an animal comprising a dose of at least $2\times10^7$ TCID50 of a modified vaccinia Ankara (MVA) virus in an oil and water emulsion, wherein the composition induces at least a 2-fold higher level of vaccinia neutralizing antibodies at 26 days after immunization when compared to the same composition in the absence of the emulsion.

2. The composition of item 1, wherein the composition induces at least a 5-fold higher level of vaccinia neutralizing antibodies at 35 days after immunization when compared to the same composition in the absence of the emulsion.

3. The composition of item 2, wherein the composition induces at least a 10-fold higher level of vaccinia neutralizing antibodies at 35 days after immunization when compared to the same composition in the absence of the emulsion.

4. The composition of any of items 1-3, wherein the emulsion is a water-in-oil emulsion.

5. The composition of any of items 1-3, wherein the emulsion is an oil-in-water emulsion.

6. The composition of any of items 1-5, wherein the emulsion comprises mannide monooleate.

7. The composition of any of items 1-6, wherein the emulsion comprises a mineral oil.

8. The composition of any of items 1-6, wherein the emulsion comprises a non-mineral oil.

9. The composition of item 7, wherein the emulsion comprises ISA 51.

10. The composition of item 8, wherein the emulsion comprises ISA720.

11. The composition of any of items 1-6, wherein the emulsion comprises squalene oil.

12. The composition of item 11, wherein the emulsion comprises sorbitan trioleate.

13. The composition of any of items 1-12, wherein the MVA is a non-recombinant MVA.

14. The composition of any of items 1-12, wherein the MVA is a recombinant MVA.

15. The composition of item 14, wherein the emulsion does not additionally contain the recombinant protein encoded by the recombinant MVA.

16. The composition of any of items 1-15, comprising a dose of at least 108 TCID50 of an MVA.

17. The composition of any of items 1-12 and 14-16, wherein the MVA comprises a nucleotide sequence comprising at least one of SEQ ID NOs 1-6.

18. The composition of any of items 1-17, wherein the animal is a human.

19. A pharmaceutical composition for inducing an immune response against a modified vaccinia Ankara (MVA) virus in an animal comprising a non-recombinant MVA in an emulsion.

20. The composition of item 19, wherein the composition induces at least a 2-fold higher level of vaccinia neutralizing antibodies at 26 days after immunization when compared to the same composition in the absence of the emulsion.

21. The composition of item 20, wherein the composition induces at least a 5-fold higher level of vaccinia neutralizing antibodies at 35 days after immunization when compared to the same composition in the absence of the emulsion.

22. The composition of any of items 19-21, wherein the emulsion comprises ISA720.

23. A pharmaceutical composition for inducing vaccinia neutralizing antibodies in an animal comprising a dose of at least $2 \times 10^7$ TCID50 of a recombinant modified vaccinia Ankara (MVA) virus in an oil and water emulsion, wherein the composition induces at least a 2-fold higher level of vaccinia neutralizing antibodies at 26 days after immunization when compared to the same composition in the absence of the emulsion inducing an immune response against a modified vaccinia Ankara (MVA) virus in an animal comprising a recombinant MVA in an oil and water emulsion, and wherein the emulsion does not additionally contain the recombinant protein encoded by the recombinant MVA.

24. The composition of item 23, wherein the composition induces at least a 5-fold higher level of vaccinia neutralizing antibodies at 35 days after immunization when compared to the same composition in the absence of the emulsion.

25. The composition of item 24, wherein the composition induces at least a 10-fold higher level of vaccinia neutralizing antibodies at 35 days after immunization when compared to the same composition in the absence of the emulsion.

26. The composition of any of items 23-25, wherein the emulsion comprises ISA720.

27. The composition of any of items 23-26, comprising a dose of at least 108 TCID50 of an MVA.

28. The composition of any of items 23-27, wherein the MVA comprises a nucleotide sequence comprising at least one of SEQ ID NOs 1-6.

29. Use of the composition of any of items 1-28 for inducing neutralizing antibodies against a modified vaccinia Ankara (MVA) virus in a human.

30. A method for inducing neutralizing antibodies against a modified vaccinia Ankara (MVA) virus in a human comprising administering a dose of the composition of any of items 1-28 to a human.

Reference will now be made in detail to exemplary embodiments, examples of which are illustrated in the accompanying drawings.

EXAMPLES

Example 1: Mice

Female BALB/cJ Rj mice from Janvier Labs (le genest saint isle, France) were approximately 7-8 weeks of age upon delivery.

Example 2: MVAs

The MVA used was MVA-BN, developed by Bavarian Nordic and deposited at ECACC under Accession No. V00083008 (see above), however, the examples are not limited to MVA-BN and also any other MVA is suitable.

The recombinant RSV and YFV viruses were generated as follows.

RSV

Origin of Inserted Genes

The coding sequence of RSV-G(A)$_{opt}$ is based on the naturally occurring glycoprotein G sequence of the RSV-A2 strain whereas RSV-G(B)$_{opt}$ is based on the RSV-B strain. The DNA sequence was codon optimized such way, that the least possible sequence homology between both glycoprotein variants exists. Both inserted genes were synthesized by GeneArt with optimized codon usage and used for cloning of the recombination plasmid pBN476. The protein sequence of RSV-G(A)$_{opt}$ shows 100% identity to GenBank sequence P03423.1. The protein sequence of RSV-G(B)$_{opt}$ shows 100% identity to GenBank sequence P20896.1.

RSV-G(A) Coding Sequence-Codon Optimized (900 bp):

(SEQ ID NO: 1)
atgagcaagaacaaggaccagcggaccgccaagaccctggaacggacct gggacaccctgaaccatctgctgttcatcagtagctgcctgtacaagct gaacctgaagtccgtggcccagatcaccctgagcatcctggccatgatc atcagcaccagcctgatcattgccgccatcatctttatcgccagcgcca accacaaagtgaccccaccacagccatcatccaggacgccacctccca gatcaagaacaccaccccacctacctgacccagaaccctcagctgggc atcagcccagcaacccagcgagatcaccagccagatcacaaccatcc tggcctccaccacccctggcgtgaagtccaccctgcagagcaccaccgt gaaaaccaagaataccaccaccacagacccagcccagcaagcccacc accaagcagagacagaacaagccccctccaagcccaacaacgacttcc acttcgaggtgttcaacttcgtgccctgcagcatctgcagcaacaaccc cacctgtttgggccatctgcaagcggatcccaacaagaagcccggcaag aaaaccacaaccaagcctaccaagaagcctaccctgaaaaccaccaaga aggaccccaagcccagaccaccaagagcaaagaggtgccaaccaccaa gcccaccgaggaacccaccatcaacaccaccaagaccaacatcatcacc accctgctgacctccaacaccaccggcaaccccgagctgacaagccaga tggaaaccttccacagcaccagcagcgagggcaaccctagccctagcca ggtgtccaccacctccgagtaccccagccagcctagcagcccccccaac accccagacagtgataa.

RSV-G(B) Coding Sequence-Codon Optimized (879 bp):

(SEQ ID NO: 2)
atgtccaagcacaagaatcagagaacagcccggacactggaaaagacat gggatacactcaatcacctgatcgtgatcagctcctgtctctaccggct caacctcaagagcattgcccagattgccctgtccgtgctggcaatgatt atttccactagtctcattatcgctgctattatcttcatcattagtgcca atcataaagtcacctcacaaccgtcaccgtgcagaccattaaaaacca taccgagaagaatatctcaacatatctgacacaggtcccccccgaaaga gtgaactcttccaaacagcccacaaccacctcccccattcataccaata gtgccacaatttctcccaacacaaagtctgaaacacaccacactactgc tcagacaaagggccgaatcaccacctctactcagaccaataagccatca acaaaatcccgctccaaaaacccacctaaaaaacctaaagatgactatc atttcgaagtctttaatttcgtcccatgttccatttgcggaaacaacca gctctgtaaatctatctgtaaaaccatcccctctaacaagccaaaaaag aaacctactattaaaccaactaataagcccaccactaagactactaaca aacgcgatccaaaaacacccgccaaaatgcctaaaaaagagatcattac aaacccagccaagaaaccaactctcaaaactaccgaacgggacacctcc atttctcagtctaccgtgctcgataccatcactcccaaatacactatcc agcagcagtcactccactcaacaacctccgagaacacccctcctcaac ccagattcctactgcttccgaaccatccaccctcaaccccaattga.

Insertion into IGR148/149:

The coding sequences for RSV-N and RSV-M2 are based on the naturally occurring sequences of the RSV-A2-strain. Both genes are connected by a well characterized 2A self-cleaving peptide sequence (2Apep) of the foot-and-mouth disease virus (FMDV) that allows the expression of two separate native proteins under the control of a single promoter. The coding sequence of RSV-F $A_{long}$ $BN_{opt}$ is based on the RSV-$A_{long}$ strain. The genes were synthesized by GeneArt with optimized codon usage and cloned into the recombination plasmid pBN475. The protein sequences of RSV-N and RSV-M2 show 100% identity to GenBank sequence P03418.1 and P04545.1, respectively. The protein sequence of RSV-F $A_{long}$ $BN_{opt}$ is 98% identical to the GenBank sequence NP_044596.1.

RSV-N 2Apep M2 Coding Sequence (1806 bp):

(SEQ ID NO: 3)
atggccctgagcaaagtgaagctgaacgacaccctgaacaaggaccagc tgctgtccagctccaagtacaccatccagagaagcaccggcgacagcat cgacaccccaactacgacgtgcagaagcacatcaataagctgtgcggc atgctgctgatcaccgaggacgccaaccacaagttcaccggcctgatcg ggatgctgtacgccatgagccggctgggccgggaggacaccatcaagat cctgcgggacgccggctaccacgtgaaggccaacggcgtggacgtgacc acccaccggcaggacatcaacggcaaagaaatgaagttcgaggtgctga ccctggccagcctgaccaccgagatccagatcaacatcgagatcgagag ccggaagtcctacaagaaaatgctgaaagaaatgggcgaggtggccccc gagtacagacgacagccccgactgcggcatgatcatcctgtgtatcg ccgcctggtcatcacaaagctggccgctggcgacagatctggcctgac cgccgtgatcagacgggccaacaacgtgctgaagaacgagatgaagcgg tacaagggcctgctgcccaaggatatcgccaacagcttctacgaggtgt tcgaaaagcaccccacttcatcgacgtgttcgtgcacttcggcattgc ccagagcagcaccagaggcggcagcagagtggagggcatcttcgccggc ctgttcatgaacgcctacggcgctggccaggtcatgctgagatggggcg tgctggccaagagcgtgaagaacatcatgctgggccacgccagcgtgca ggccgagatggaacaggtggtggaggtgtacgagtacgcccagaagctg ggcggcgaggccggcttctaccacatcctgaacaacccaaggcctccc tgctgtccctgacccagttcccccactttagcagcgtggtgctcggaaa tgcagccggactgggcatcatgggcgagtaccgcggcacccccagaaac caggacctgtacgacgccgccaaggcctacgccgagcagctgaaagaaa acggcgtgatcaactacagcgtgctggacctgacagccgaggaactgga agccattaagcaccagctgaaccctaaggacaacgacgtggagctgaac ttcgatctgctgaaactggccggcgacgtggaaagcaaccctggcccca gcagacggaaccctgcaagttcgagatccggggccactgcctgaacgg caagcggtgccacttcagccacaactacttcgagtggcccctcatgct ctgctggtccggcagaactttatgctgaaccggatcctgaagtccatgg acaagagcatcgataccctgagcgagatcagcggagccgccgaactgga tagaaccgaggaatacgccctgggcgtggtcggagtgctggaaagctac atcggcagcatcaacaacatcaccaagcagagcgcctgcgtggccatga gcaagctgctgaccgagctgaacagcgacgatatcaagaagctgcgcga caacgaagaactgaactcccccaagatccgggtgtacaacacagtgatc agctacattgagagcaaccggaagaacaacaagcagaccatccatctgc tgaagcggctgcccgccgacgtgctgaaaaagaccatcaagaacaccct ggacatccacaagtccatcaccatcaataaccccaaagaaagcaccgtg tccgacaccaacgaccacgccaagaacaacgacaccacctga.

RSV-F-$A_{long}$ $BN_{opt}$ Coding Sequence (1725 bp):

(SEQ ID NO: 4)
atggaactccctattctcaaagccaatgctattactaccattctcgccg ctgtcacctttttgtttcgcctcttcccagaatattaccgaagagtttta ccagtctacctgttccgccgtcagtaaaggatacctgtccgccctccgc actggttggtatactagtgtcattacaatcgaactctcaaatataaaag aaaataagtgtaatgggaccgatgctaaagtcaaactcattaaacaaga actcgataagtataagaatgctgtcactgagctgcaactgctgatgcag tctacacccgcagccaataatcgagccagacgcgagctgcctcgcttta tgaattatactctcaataatactaaaaagacaaacgtcaccctcagtaa aaagcgaaaagacggtttctcggattcctcctcggcgtgggctctgct atcgctagcggaattgctgtctccaaagtcctccatctggaaggggagg tcaacaaaattaagtctgctctcctctctacaaacaaagccgtcgtgtc tctctccaatggcgtgtctgtgctcacctctaaagtgctcgacctcaaa aattacattgataaacagctgctccctattgtgaacaaacagtcttgcc gcattagcaatatcgaaaccgtcattgaatttcaacaaaagaataatag gctcctcgaaattacccgcgaattctccgtgaatgtgggagtcacaaca cctgtctctacctatatgctcactaactccgaactcctctccctcatta acgatatgccattacaaatgatcagaaaaactcatgtctaataacgt ccagattgtccgccagcagtcttatagcattatgtccattatcaaagag gaagtcctcgcttacgtcgtccagctccctctgtatggggtcatcgata -continued

```
caccttgttggaaactccatacctccccactgtgtacaaccaataccaa agaagggtccaatatttgcctgacaagaaccgaccgcgggtggtactgt gataatgccggctctgtctccttttcccccaggccgaaacctgtaaag tccagtctaatcgagtcttttgcgatactatgaattccctcaccctccc ttcagaagtgaatctctgtaacgtcgatattttcaaccctaaatatgat tgcaaaattatgaccagtaaaactgacgtgtcctcttccgtcatcacct ccctcggtgctattgtgtcttgttacggaaaaactaaatgcacggctag taataagaaccgaggcattattaagaccttttccaacggctgtgattat gtgtctaacaaaggcgtggatactgtcagtgtcggaaatacactctact atgtcaacaaacaggaagggaaaagtctctacgtcaaaggggagccgat aatcaattttacgatccctcgtctttccctccgatgaatttgatgcc agtatttcccaggtgaacgaaaaaatcaatcagtccctcgcttttatta gaaaatctgatgaactcctgcataatgttaacgctggcaagagtaccac aaacatcatgatcaccaccatcatcatcgtgatcattgtgatcctgctg agtctgatcgccgtgggcctgctgctgtactgcaaggcccgcagcaccc ctgtgaccctgtccaaggatcagctgtccggcatcaacaatatcgcctt ctccaactga.
```

Origin of Inserted Promoters

The promoter PrS is a synthetic promoter designed from consensus sequences of early and late elements of Vaccinia virus promoter (Chakrabarti et al., BioTechniques 23:1094-1097 (1997)). In the final recombination plasmid pBN476 (IGR 64/65) the PrS promoter was inserted upstream of RSV-G(B)$_{opt}$. Consequently, RSV-G(B)$_{opt}$ will be expressed during early as well as late phases of infection of the recombinant virus MVA-mBN294B.

The promoter Pr7.5e/l of the Vaccinia virus 7.5 kDa gene is an early and late promoter (Cochran et al., J Virol 54: 30-37 (1985)). In the final recombination plasmid pBN476, the Pr7.5e/l-promoter was inserted upstream of the RSV-G (A)$_{opt}$ coding sequence. Consequently, RSV-G(A)$_{opt}$ will be expressed during the early as well as late phase of infection of the recombinant virus MVA-mBN294B.

The promoter PrH5m (Wyatt et al., Vaccine 14:1451-1458 (1996) is a modified version of the Vaccinia virus H5 gene promoter (Wennier et al., PLoS ONE 8(8): e73511 (2013)). It consists of strong early and late elements resulting in the expression of RSV-F-A$_{long}$ BN$_{opt}$ during both, early and late phases of infection of the recombinant virus MVA-mBN294B.

The promoter PrLE1 (=pHyb) is a synthetic promoter (Baur et al., J Virol 84:8743-8752 (2010)) consisting of the A-type inclusion body promoter of cowpox virus (ATI promoter), a late promoter fused to five optimized early elements of Pr7.5. PrLE1 was shown to induce especially strong cell mediated immune responses. Consequently, the gene encoding for RSV-N and RSV-M2 (N_2Apep_M2) will be expressed during early as well as late phase of infection of the recombinant virus MVA-mBN294B.

Construction of the Recombination Plasmids pBN475 and pBN476

Figure 11:
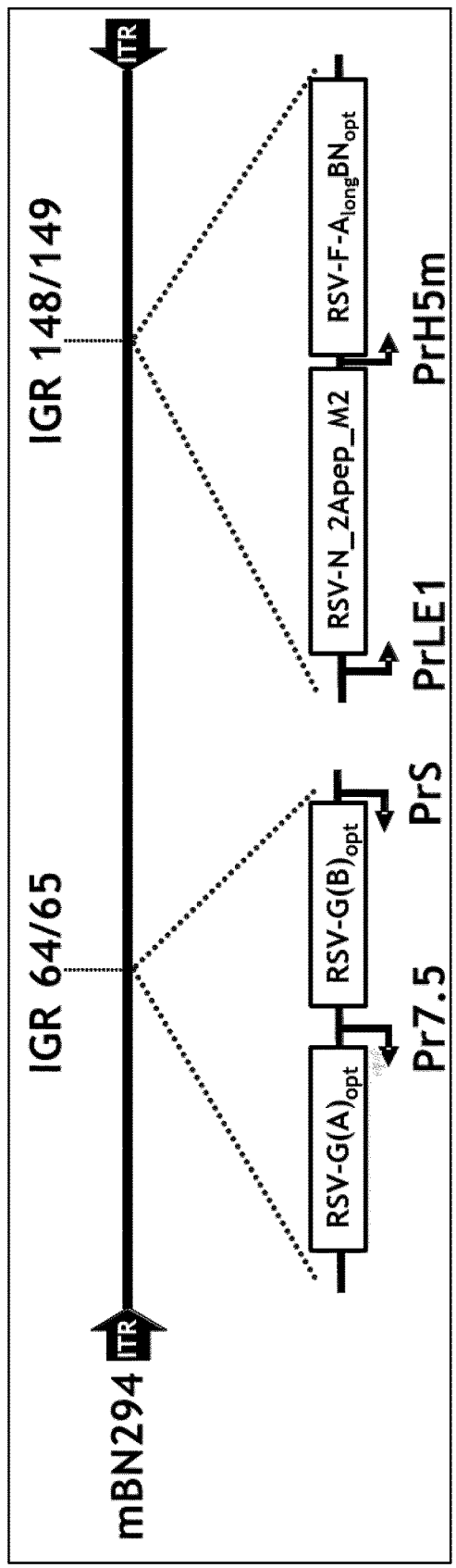
FIG. 11 depicts a Schematic map of MVA-BN genome outlining the sites used for generation of MVA-mBN294B (IGR 64/65, IGR 148/149).

CEF cells were infected with MVA-BN and subsequently transfected with the appropriate recombination plasmid. During homologous recombination, the plasmid flanking sequences recombine with the homologous sequences of the insertion site in the MVA-BN virus genome. This targets the insertion of the plasmid sequences into the respective site (e.g., IGR 148/149) of the MVA-BN genome (FIG. 11). The presence of a selection cassette in the inserted sequence allows for positive selection of recombinant viruses.

Recombination Plasmid pBN475

Figure 12:
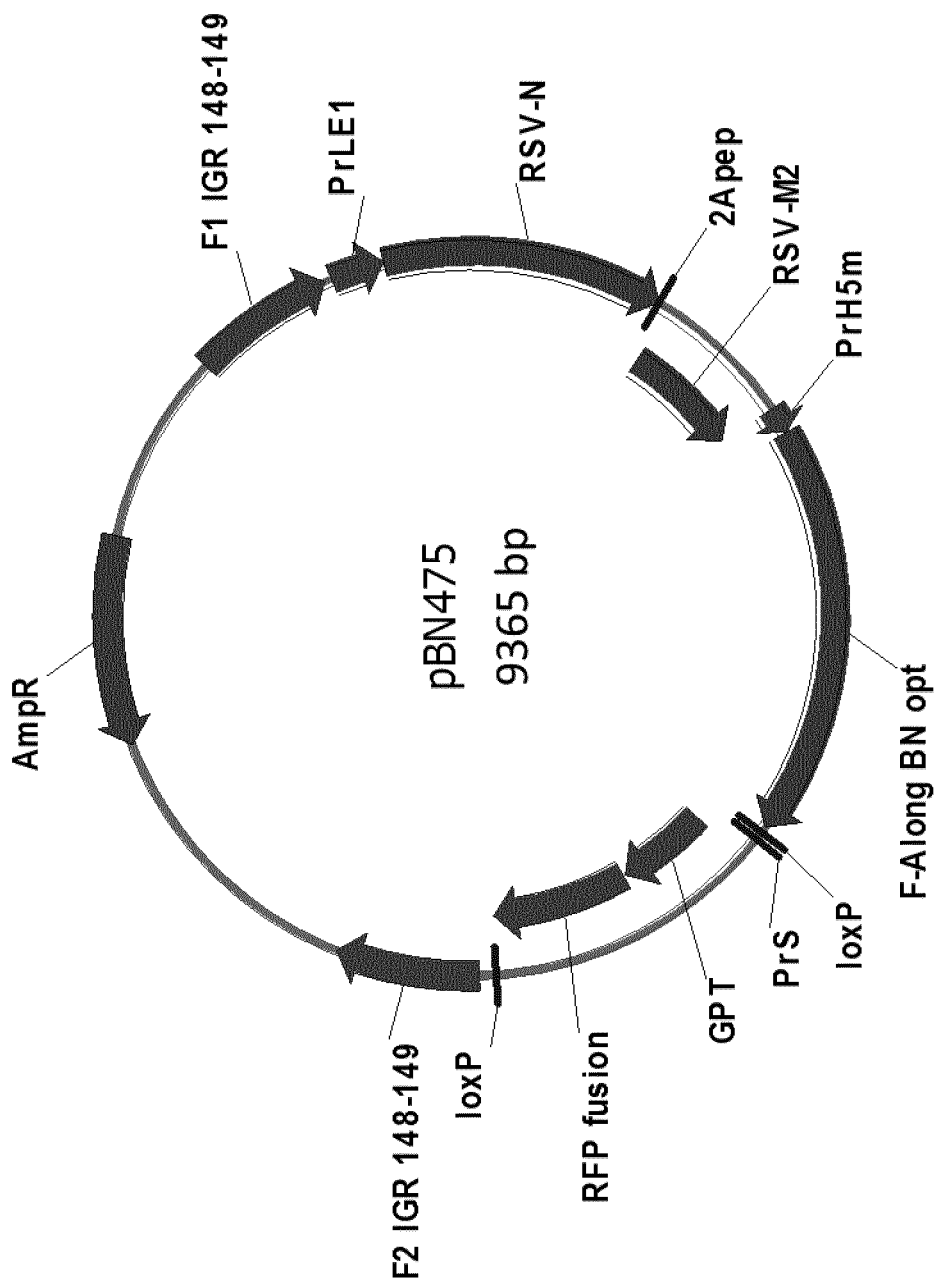
FIG. 12 depicts Recombination Plasmid pBN475. The RSV-N and M2 genes linked by 2Apep cleavage site (N_2Apep_M2), under control of the PrLE1 promoter (which is identical to pHyb in Baur et al., *J. Virol.* 84:8743-52 (2010)), were inserted into the MluI/PmeI restriction enzyme site of pBN474 REF8.9 containing the RSV F-Along BNopt transgene, already. In addition, the plasmid contains MVA-BN DNA sequences flanking the IGR 148/149 of the MVA-BN genome and a loxP flanked selection cassette. The loxP sites allow the later elimination of the selection cassette by CRE-recombinase mediated recombination.

For generation of MVA-mBN294B the final recombination plasmid pBN475 (FIG. 12) was constructed, comprising the RSV genes N and M2 (N_2Apep_M2) under the control of the PrLE1 (=pHyb) promoter and F-A$_{long}$ BN$_{opt}$ driven by the PrH5m promoter, and generated by gene synthesis. Sub-sequential cloning resulted in the final recombination plasmid pBN475.

Recombination Plasmid pBN476

Figure 13:
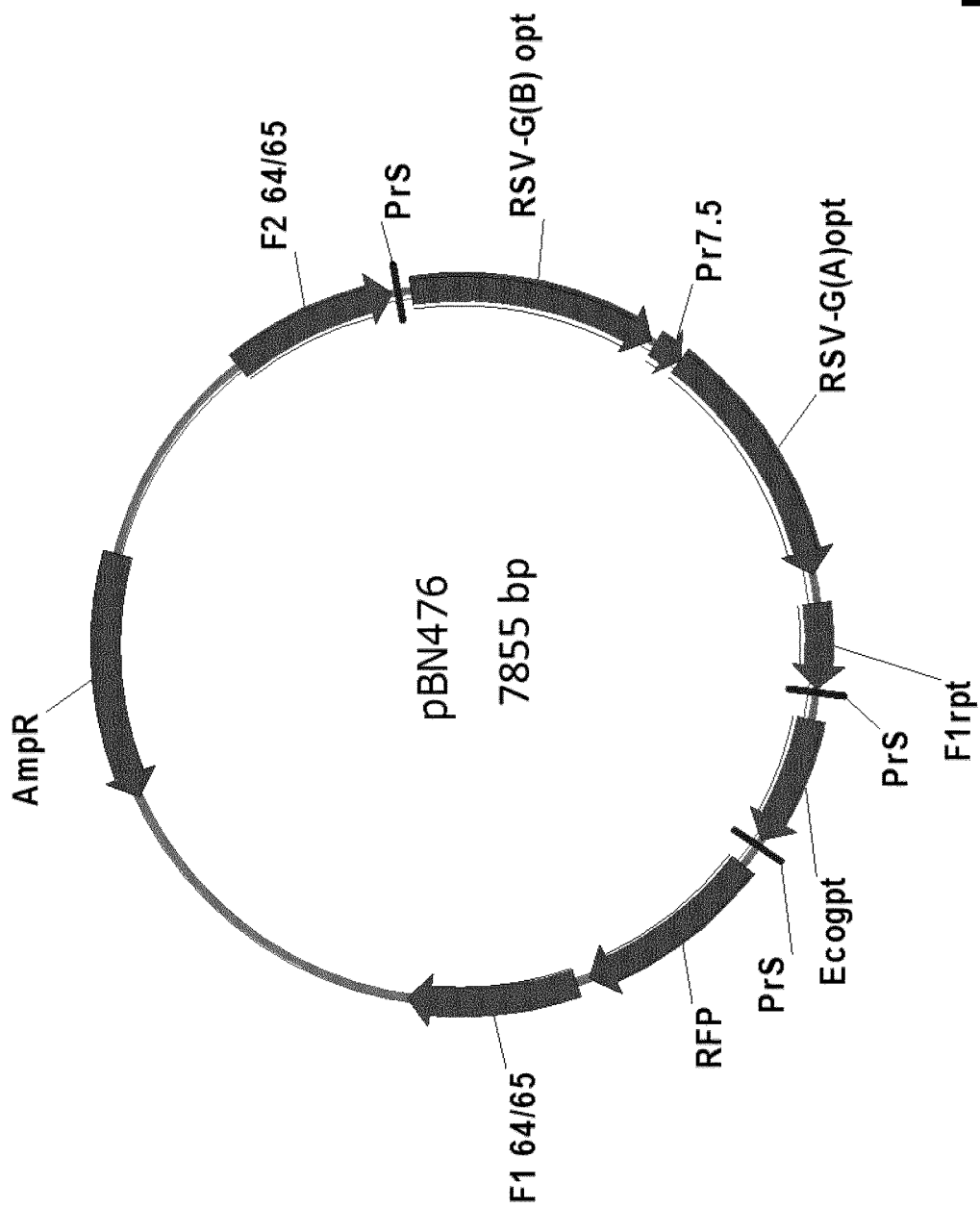
FIG. 13 depicts Recombination Plasmid pBN476. The RSV gene G(B)opt, driven by the PrS promoter, was inserted into the NheI/BspEI restriction enzyme site of pBN473 REF8.11 containing the RSV G(A)opt transgene under control of the Pr7.5e/I promoter, already. In addition, the plasmid contains MVA-BN DNA sequences flanking the IGR 64/65 of the MVA-BN genome and the selection cassette.

For generation of MVA-mBN294B the final recombination plasmid pBN476 (FIG. 13) was constructed, comprising the RSV genes G(B)$_{opt}$ and G(A)$_{opt}$ driven by the PrS and Pr7.5 promoters, respectively and generated by gene synthesis. Sub-sequential cloning resulted in the final recombination plasmid pBN476.

Removal of the Selection Cassette

Figure 14:
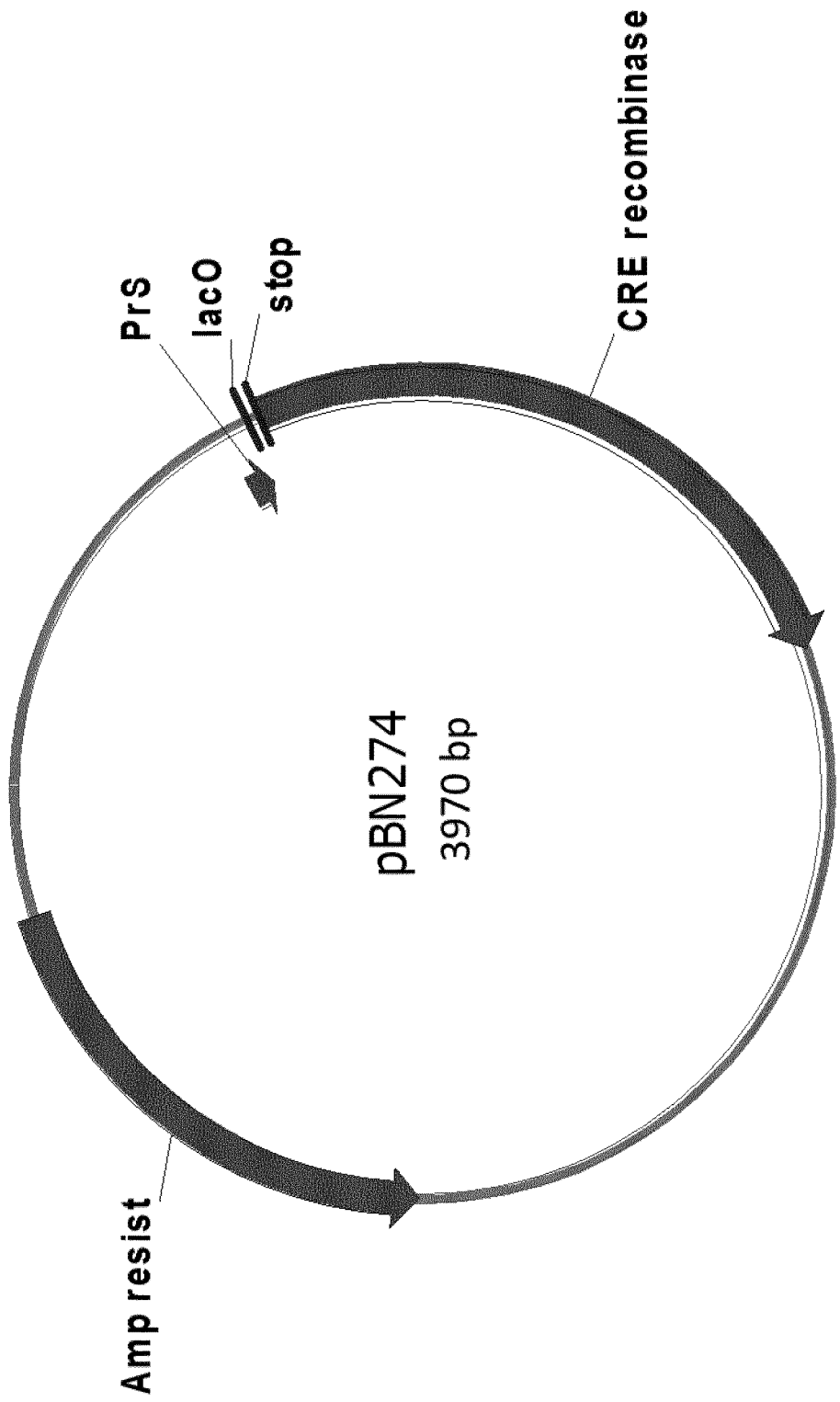
FIG. 14 depicts an Expression Plasmid Encoding the Site Specific CRE-recombinase. The CRE-recombinase is targeting specifically the loxP sites.

For the generation of recombinant MVA-mBN294B the cre/loxP system was used to remove the selection cassette inserted with pBN475 via homologous recombination. Therefore CEF cells were transfected with an expression plasmid encoding the CRE-recombinase (pBN274; FIG. 14). pBN274 is a pBluescript based plasmid including the ORF of CRE recombinase placed under control of the poxvirus specific PrS promoter. To avoid readthrough in bacteria or eukaryotic cells from cryptic promoter elements, three stop codons in all three reading frames as well as a lacO operator sequence are introduced upstream of the CRE ORF. The CRE-recombinase is a site specific recombinase, which catalyzes the precise excision of all DNA sequences flanked by their target sequence loxP, therefore leading to complete removal of the selection cassette. The passages of the recombinant virus on CEF cells transfected with the CRE expression plasmid pBN274 was repeated until no selection cassette could be detected by sensitive PCR.

Generation of Recombinant MVA-mBN294B

To create the recombinant Vaccinia virus MVA-mBN294B expressing the RSV-proteins F-A$_{long}$ BN$_{opt}$, G(A)$_{opt}$, G(B)$_{opt}$, N and M2 the recombination plasmids pBN475 and pBN476 were constructed as described above. Prior to MVA-mBN294B generation, the two parental viruses MVA-mBN293A, containing the RSV transgenes F-A$_{long}$ BN$_{opt}$, N and M2, and MVA-mBN302B, containing the RSV transgenes G(A)$_{opt}$ and G(B)$_{opt}$, were established.

During generation of the parental virus MVA-mBN302A, primary CEF cells were infected with MVA-BN and subsequently transfected with the recombination plasmid including the RSV transgenes G(A)$_{opt}$ and G(B)$_{opt}$ flanked by IGR64/65. After amplification and plaque purification (twelve passages; four of them including plaque purification) under selective conditions (mycophenolic acid, xanthine and hypoxanthine) the recombinant MVA-BN product designated MVA-mBN302A P12PP4#41 (InterimPremaster A) was obtained. The selection cassette was removed after further amplification and plaque purification under non selective conditions and a clone was expanded (MVA-mBN302B P7PP2#66) which was shown to be free of the selection cassette twice before starting the generation of MVA-mBN294A.

The steps performed during generation of the second parental virus MVA-mBN293A were analogous to those undertaken during generation of the parental virus MVA-mBN302A with thirteen passages, four of them including plaque purification under the same selective conditions as MVA-mBN302A, resulting in the recombinant virus MVA-mBN293A P13PP4#65 (InterimPremaster A) containing the RSV transgenes F-A$_{long}$ BN$_{opt}$, N and M2 (N_2Apep_M2) flanked by IGR148/149.

To generate the final virus MVA-mBN294A, primary CEF cells were co-infected with a mixture of both parental viruses using 2.5 times more MVA-mBN302B (P7PP2#66) than MVA-mBN293A (P13PP4#65), still possessing the selection cassette. Cells were infected for 2.5 hours at 30° C., washed and incubated with media containing selective conditions (mycophenolic acid, xanthine and hypoxanthine), immediately. After amplification and plaque purification (nine passages; four of them including plaque purification) the recombinant MVA-BN product MVA-mBN294A P9PP4#86 (InterimPremaster A), containing the RSV transgenes G(A)$_{opt}$ and G(B)$_{opt}$ flanked by IGR64/65 and F-A$_{long}$ BN$_{opt}$, N, M2 (N_2Apep_M2) flanked by IGR148/149, was obtained. The selection cassette was removed after further amplification and plaque purification under non selective conditions (eighteen passages; six of them including plaque purification) resulting in the recombinant virus MVA-mBN294B P18PP6#153 (Premaster B) devoid of the selection cassette which was used for amplification of the final recombinant virus MVA-mBN294B # MVB31A12.

At all stages, VP-SFM serum free medium was used.

Yellow Fever

Origin of Inserted Genes

The coding region of M and E, based on the naturally occurring sequence of YFV (NCBI Accession No NC_002031), were codon optimized for higher expression and to avoid interfering DNA and RNA signal sequences (the amino acid sequence is 100% identical to NCBI Accession No. NP_041726.1) and inserted into the MVA-BN backbone. For optimal processing the poly-protein PreM-E possesses the pro-peptide of the C protein which function as an anchor for the endoplasmatic reticulum. The precursor PreM-E eventually will be cleaved by a host signal peptidase. PreM in addition is cleaved in the Golgi apparatus by a furin-like cellular peptidase resulting in the un-glycosylated protein M.
PreM-E (2037 bp)

The optimized Yellow fever virus PreM and E Sequences in pBN501 are shown below. The start codon (ATG) and the stop codon (TGA) are shown at the beginning and end of the sequence.

```
                                        (SEQ ID NO: 5)
atgagccacgacgtgctgaccgtgcagttcctgatcctgggcatgctgc tgatgacaggcggcgtgacactcgtgcggaagaacagatggctgctgct gaacgtgaccagcgaggacctgggcaagaccttctctgtgggcaccggc aactgcaccaccaacatcctggaagccaagtactggtgcccgacagca tggagtacaactgcccaacctgagcccagagaggaacccgacgacat cgactgctggtgctacggcgtggaaaacgtgcgggtggcctacggcaag tgcgatagcgccggcagaagcagaagaagcaggcgggccatcgacctgc ccacccacgaaaaccacggcctgaaaacccggcaggaaaagtggatgac cggccggatgggcgagcggcagctgcagaaaattgagcggtggtttgtg cggaacccttcttcgccgtgaccgccctgacaatcgcctacctcgtgg gcagcaacatgacccagagagtcgtgatcgccctgctggtgctggctgt gggccctgcctatagcgcccactgtatcggcatcaccgaccgggacttc atcgagggcgtgcacggcggaacatgggtgtccgctaccctggaacagg ataagtgcgtgaccgtgatggccccccgacaagcccagcctggacatcag cctggaaaccgtggccatcgatagacccgccgaagtgcggaaagtgtgc tacaacgccgtgctgacacacgtgaagatcaacgacaagtgccccagca ccggcgaagcccacctggccgaagagaacgagggcgacaacgcctgcaa gcggacctacagcgatagaggctggggcaatggctgcggcctgtttggc aagggcagcatcgtggcctgcgccaagttcacctgtgccaagagcatga gcctgttcgaggtggaccagaccaagatccagtacgtgatccgggccca gctgcacgtgggagccaagcaggaaaactggaacaccgacatcaagacc ctgaagttcgacgccctgagcggctcccaggaagtggaattcatcggct atggcaaggccaccctggaatgccaggtgcagaccgccgtggacttcgg caacagctatatcgccgagatggaaaccgagagctggatcgtggaccgg cagtgggctcaggatctgaccctgccttggcagtctggctctggcggag tgtggcgggaaatgcaccacctggtggaattcgagcctcccacgccgc caccattagagtgctggccctgggcaatcaggaaggctctctgaaaaca gccctgaccggcgccatgagagtgaccaaggacaccaacgacaacaacc tgtacaagctgcatggcggccacgtgtcctgcagagtgaagctgtctgc cctgacactgaagggcaccagctacaagatctgcaccgacaagatgttc ttcgtgaagaacccaccgacaccggccacgcacagtcgtgatgcaag tgaaggtgtccaagggcgctccctgccggatccctgtgatcgtggccga tgatctgacagccgccatcaacaagggcatcctcgtgacagtgaaccct atcgcctccaccaacgatgacgaggtgctgatcgaagtgaacccccct tcggcgactcctacatcatcgtgggacggggcgacagcagactgaccta ccagtggcacaaagagggcagcagcatcggcaagctgttcacccagacc atgaagggcgtggaacggctggccgtgatgggagataccgcctgggatt tcagcagcgctggcggcttctttaccagcgtgggcaagggaatccacac cgtgttcggcagcgccttccagggactgttcggcggcctgaactggatc accaaagtgatcatgggcgctgtgctgatctgggtgggaatcaacaccc ggaacatgaccatgagcatgtccatgatcctcgtgggagtgattatgat gttcctgtccctgggcgtgggcgcctga.
```

A recombinant MVA-BN construct encoding the YF virus reading frame PreM-E (FIG. 15), which is essential for inducing protective immunity, was constructed. The reading frame PreM-E includes the following YF sequences:
- The endoplasmatic reticulum (ER) anchor of the YF virus capsid protein C (amino acid 102-122 of YF virus)
- The Pre-M protein, which is the precursor of the membrane anchored small envelope protein M.
- The envelope protein E, which is responsible for the attachment to the target cell surface in the natural virus-host interaction followed by subsequent fusion after internalization of the virion by endocytosis.

Both the ER anchor and the M protein are essential for processing and maturation of the YF virus particle, the ER anchor being responsible for incorporation of the polyprotein into the ER membrane, which is cleaved by a host signal peptidase thereafter and the precursor PreM forming a complex with the E protein in the ER, which, after cleavage of Pre-M by the cellular protease furin in the golgi-apparatus, is released from the complex. This enables the dimerization of E resulting in the formation of infectious viral particles, as well as non-infectious virus-like particles (VLP). Immunity to YF virus is primarily provided by neutralizing antibodies directed against epitopes of the E protein.

For the generation of MVA-BN-YF, the MVA-BN seed stock corresponding to passage 598 was used as starting material.

The coding region of M and E, based on the naturally occurring sequence of YF Virus (YFV) (NCBI Accession No. NC_002031), were codon optimized to avoid cryptic DNA and RNA signals and to allow for higher expression and inserted into the MVA-BN backbone. The original Amino acid sequence was maintained and is 100% identical to NCBI Accession No. NP_041726.1. For optimal processing the polyprotein PreM-E possesses the propeptide of the C protein which function as an anchor for the endoplasmatic reticulum.

Origin of Inserted Promoters
PrH5m-Promoter

The promoter PrH5m (BN1) is a modified version of the Vaccinia virus H5 gene promoter. It consists of strong early and late elements resulting in the expression of YFV PreM-E during both, early and late phases of infection of the recombinant virus MVA-mBN314B. The DNA Sequence of PrH5m (BN1) Promoter is: 5' taaaaattgaaaataaatacaaaggt-tcttgagggttgtgttaaattgaaagcgagaaataatcataaataataattatcgcg atatccgttaagtttgtatcgta 3' (SEQ ID NO:6).

Construction of the Recombination Plasmids pBN501

Figure 15:
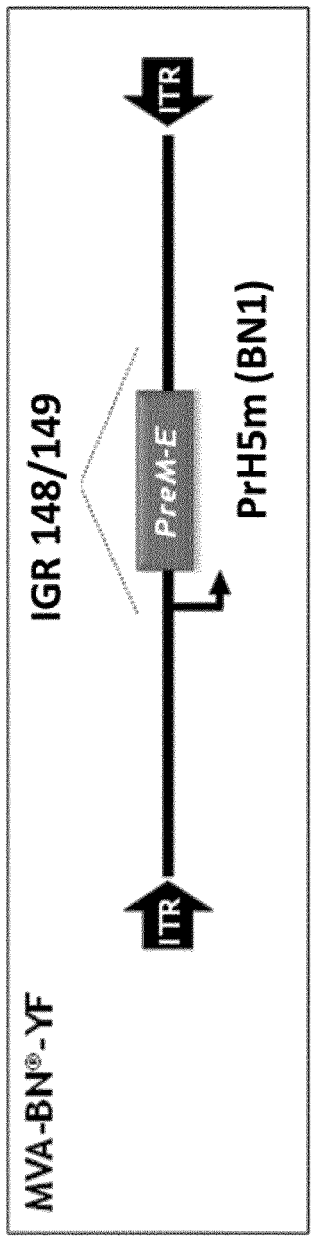
FIG. 15 depicts a Schematic Map of the Recombinant Insert (PreM-E) in MVA-BN®-YF.
Figure 16:
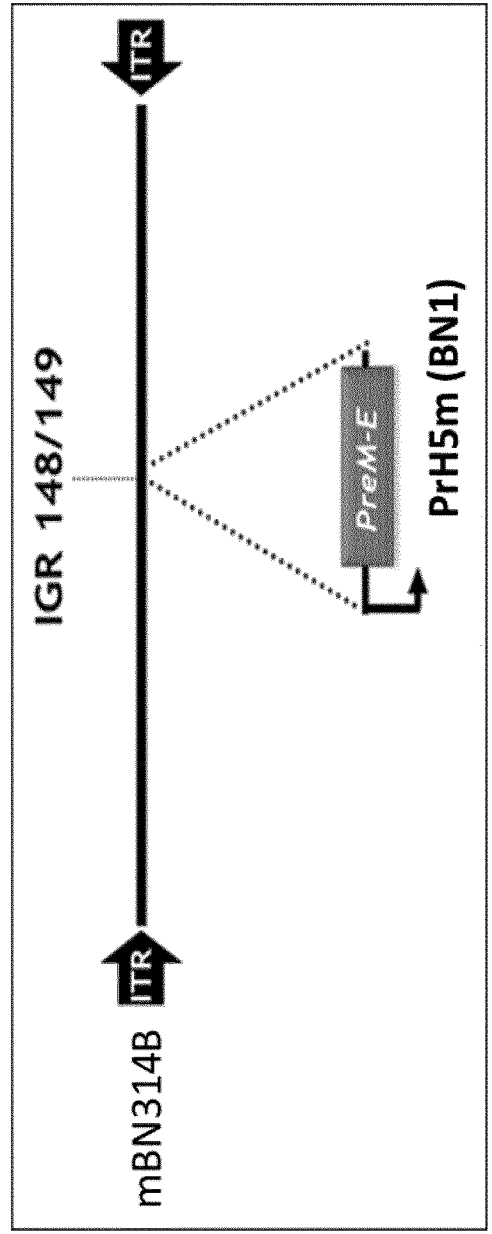
FIG. 16 depicts a Schematic map of MVA-BN genome outlining the IGR 148/149 sites used for generation of MVA-mBN314B.

CEF cells were infected with MVA-BN and subsequently transfected with the appropriate recombination plasmid. During homologous recombination, the plasmid flanking sequences recombine with the homologous sequences of the insertion site in the MVA-BN virus genome. This targets the insertion of the plasmid sequences into the respective site (e.g., IGR 148/149) of the MVA-BN genome (FIG. 15). The presence of a selection cassette in the inserted sequence allows for positive selection of recombinant MVA-BN viruses.

Recombination Plasmid pBN501

Figure 17:
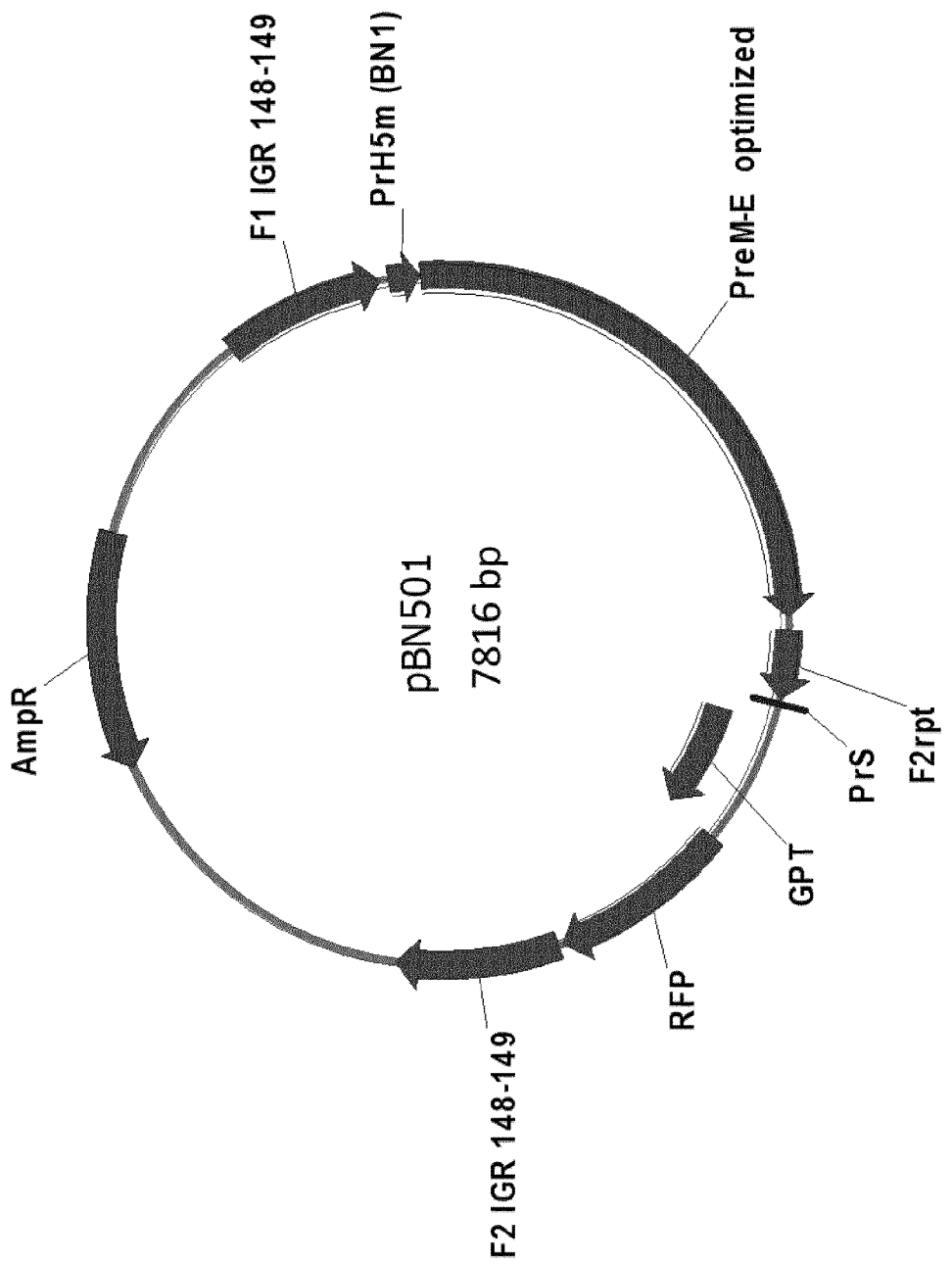
FIG. 17 depicts Recombination Plasmid pBN501. The PreM-E was inserted under control of the promoter PrH5m into the MluI/NheI site of pBNX205 REF8.6. In addition the plasmid also contains MVA-BN DNA sequences flanking the IGR 148/149 of the MVA-BN genome (F1 and F2 IGR148/149), as well as a repetitive sequence of the IGR148/149 Flank 2 (IGR148/149 F2rpt) for later excision of the selection cassette.

To generate MVA-mBN314B the final recombination plasmids pBN501 (FIG. 17) was constructed. The insert fragment of pBN501 carrying PreM and E of YFV under the control of the PrH5m (BN1) promoter was generated by gene synthesis. Sub sequential cloning resulted in the final recombination plasmid pBN501.

Generation of Recombinant MVA-mBN314B

To create a recombinant Vaccinia virus expressing YFV PreM-E, the recombination plasmid pBN501 was constructed as described as above. Primary CEF cells were infected with MVA-BN (MOI 1.0) and subsequently transfected with the recombination plasmid. After amplification and plaque purification (eleven passages; three of them including plaque purification) under selective conditions (mycophenolic acid/xanthine and hypoxanthine) the recombinant MVA-BN product designated MVA-mBN314A P14PP4#34, containing the genes for PreM and E proteins of YFV was obtained.

After further amplification, removal of the selection cassette under non-selective conditions and plaque purification under non selective conditions (twenty one passages; seven of them including plaque purification) the recombinant virus MVA-mBN314B P21 PP7#116 devoid of selection cassette could be isolated.

At all stages, VP-SFM serum free medium was used.

Both recombinant viruses were propagated and titrated on primary chicken embryo fibroblasts that were prepared from 11-day-old embryonated, pathogen-free hen eggs (Charles River, Mass., USA) and cultured in RPMI-1640 medium. All viruses were purified through a sucrose cushion.

Example 3: Immunization

Either $5\times10^8$ $TCID_{50}$ MVA or recombinant MVA were mixed with oil adjuvant to obtain an emulsion just prior administration. 250 µl of the emulsion was injected in the left side of the inguinal region and 250 µl was injected in the right side. For administration of the $\frac{1}{10}$ dose, 50 µl of the emulsion was injected either in the left of right side of the inguinal region. Mice were administered at Day 0. Some were boosted either 21 or 28 days later.

Example 4: ELISA

Vaccinia-specific serum mouse IgG titers were measured by direct ELISA as described previously. Garza et al., *Vaccine* 27, 5496-5504 (2009). Briefly, 96-well plates were coated overnight with MVA antigen. Test sera were titrated using twofold serial dilutions starting at 1:50. A sheep anti-mouse IgG-HRP (AbD Serotec) was used as detection antibody. The antibody titers were calculated by linear regression and defined as the serum dilution that resulted in an optical density of 0.30 at $OD_{450}$.

RSV-specific serum mouse IgG titers were measured by direct ELISA. Briefly, 96-well plates were coated overnight with RSV Grade 2 Antigen, Meridian. Test sera were titrated using two-fold serial dilutions starting at 1:50. A sheep anti-mouse IgG-HRP (AbD Serotec) was used as detection antibody. The antibody titers were calculated by 4-parameter fit and defined as the serum dilution that resulted in an optical density of 0.50 at $OD_{450}$.

Vaccinia-specific serum rabbit IgG titers were measured by direct ELISA. Briefly, 96-well plates were coated overnight with MVA antigen. Test sera were titrated using twofold serial dilutions starting at 1:50. Monoclonal anti rabbit IgG Peroxidase (Sigma) was used as detection antibody. The antibody titers were calculated by linear regression and defined as the serum dilution that resulted in an optical density of 0.20 at $OD_{450}$.

Example 5: Plaque Reduction Neutralization Test (PRNT) Assay

Vaccinia-based PRNT assay was performed as described in Garza et al. *Vaccine* 27, 5496-5504 (2009). Briefly, heat-inactivated sera were serially diluted and incubated with vaccinia virus Western Reserve (Advanced Biotechnologies Inc.). After incubation the mixtures were allowed to adsorb on Vero cells for 70 minutes. Then, overlay medium was added and plates were incubated for 24 hours. After staining with Crystal Violet, the neutralizing titer was determined as the serum dilution which was able to neutralize 50% of the mature virus.

The Yellow fever virus PRNT assay was performed as described in Schafer et al. *PLoS One*. 2011; 6(9):e24505 (September 2011). Briefly, heat-inactivated sera were serially diluted and incubated with Yellow fever virus (STAMARIL® commercial Yellow Fever vaccine, Sanofi Pasteur). After incubation the mixtures were allowed to adsorb on Vero cells for 90 minutes. Then, overlay medium was added and plates were incubated for 72 hours. After immunostaining and developing with DAB Liquid Buffer Solution, the neutralizing titer was determined as the first serum dilution which was able to neutralize 50% of the mature virus.

The RSV Plaque Reduction Neutralization Test (PRNT) assay was performed as follows. Heat-inactivated sera were serially diluted and incubated with RSV virus (Approximately 100 pfu RSV-A2). After incubation the mixtures were allowed to adsorb on Vero cells for 70 minutes. Then, overlay medium was added and plates were incubated for 5 days. After staining with Crystal Violet, the neutralizing titer was determined as the serum dilution which was able to neutralize 50% of the mature virus.

Example 6: ELISpot

After erythrolysis, splenocytes were stimulated 20 hours with either an MVA-specific peptide (F2L 26-34, SPYAAGYDL (SEQ ID NO:7) at a concentration of 5 µg/ml or 0.5 µg/ml Concanavalin (ConA) and IFNγ-secreting cells were detected by ELISpot assay (BD Biosciences). The stimulation index was obtained by subtracting the number of unspecific spots from non-stimulated cells from the number of spots obtained with the specific stimulation.

Example 7: Vaccinia-Specific IgG Titers with $10^8$ MVA in Oil and Water Emulsion Mice were immunized subcutaneously (s.c.) either once (Day 0) or twice (Days 0 and 28) with $1\times10^8$ TCID$_{50}$ of MVA-BN alone or in emulsion (0.5 ml) with either ISA51 or ISA720 at a ratio of 23:77 (W/O). Control mice were immunized twice s.c. with TBS. Sera was obtained prior the first immunization and then on Days 7, 14, 26, 35, 56 and 98 post immunization. Vaccinia-specific IgG titers were determined by ELISA. The results are shown in FIG. 1. Unexpectedly, a 5 to 10-fold increase in vaccinia-specific IgG titers was seen with the oil and water emulsions.

Figure 2:
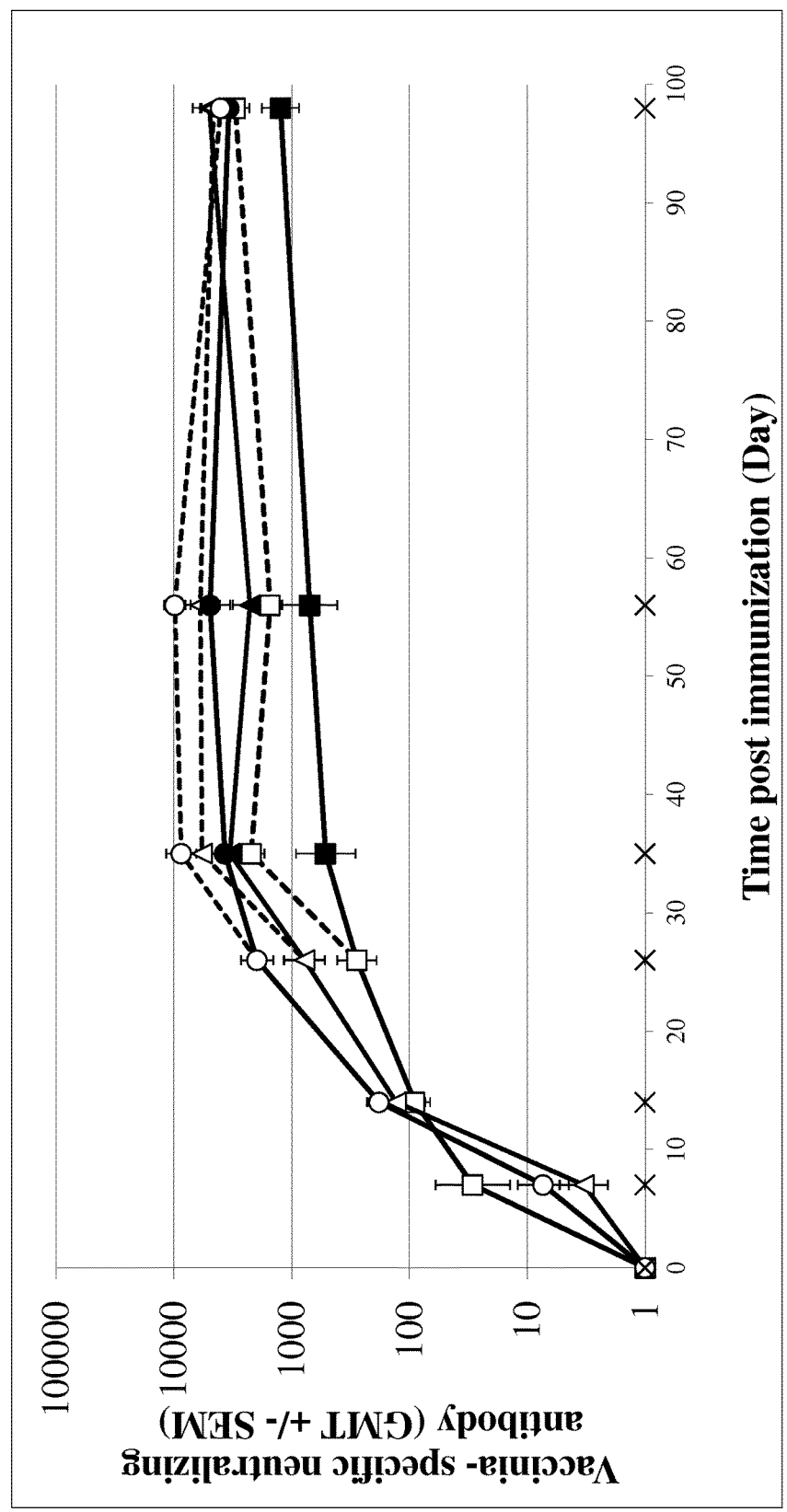
FIG. 2 depicts serum vaccinia-specific neutralizing antibody responses measured by PRNT after immunization with a dose of $10^8$ non-recombinant MVA in an oil and water emulsion. The Figure legend for each graph in FIG. 2 is the same as shown in FIG. 1.

Example 8: Vaccinia-Specific Neutralizing Antibody Responses with $10^8$ MVA in Oil and Water Emulsion To determine whether this increase in vaccinia-specific IgG titers was associated with a similar increase in neutralizing antibody titers, the effect of the oil and water emulsions on neutralizing antibody titers was assessed. Mice that were immunized subcutaneously (s.c.) either once (Day 0) or twice (Days 0 and 28) with $1\times10^8$ TCID$_{50}$ of MVA-BN alone or in emulsion (0.5 ml) with either ISA51 or ISA720 at a W/O ratio of 23:77 were analyzed for vaccinia-specific neutralizing antibody responses by PRNT. The results are shown in FIG. 2. Unexpectedly, a 2 to 7-fold increase in vaccinia-specific neutralizing antibody titers was seen with the oil and water emulsions.

Figure 3:
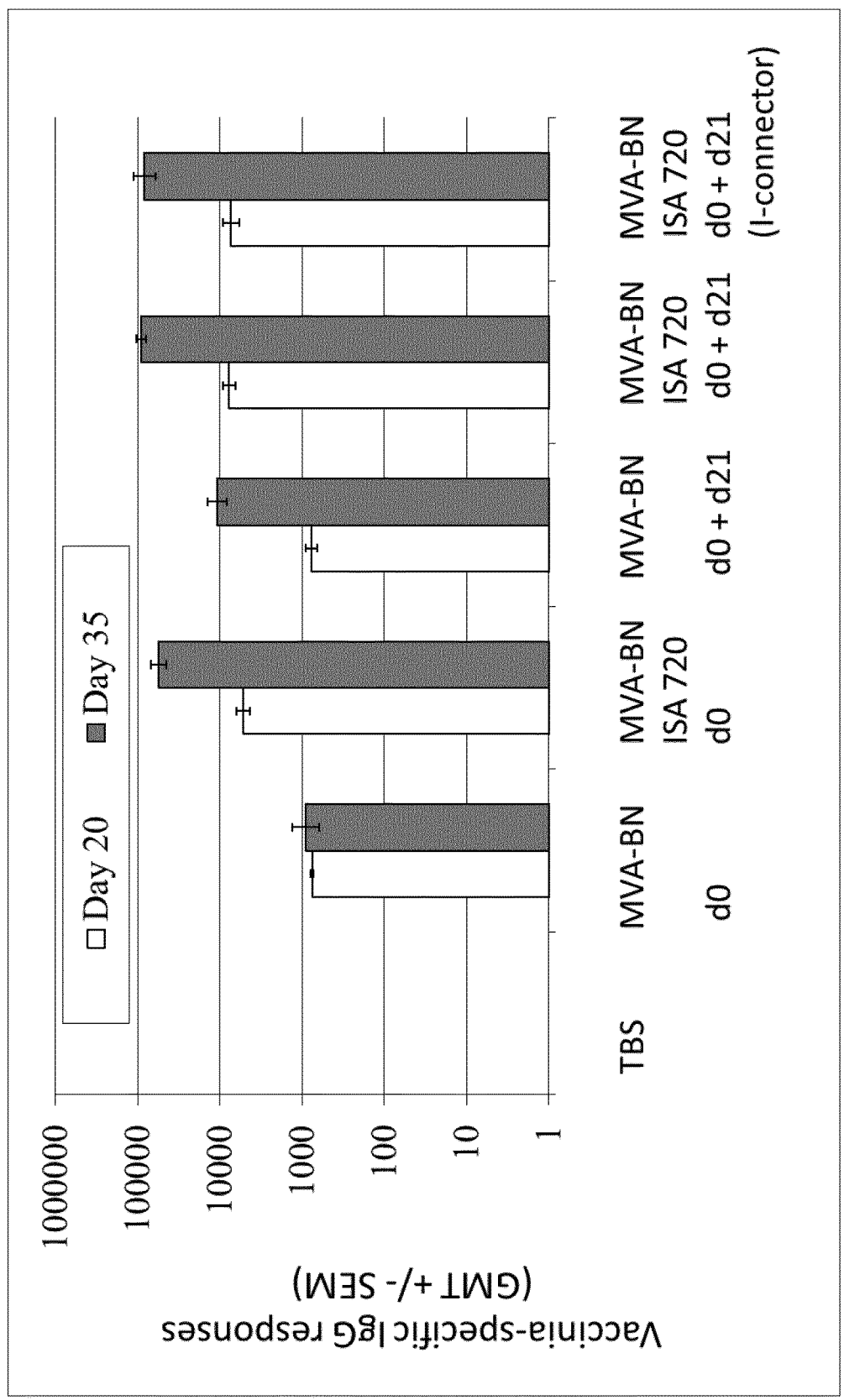
FIG. 3 depicts serum vaccinia-specific IgG antibody responses measured by ELISA after immunization with a recombinant MVA in an oil and water emulsion.

Example 9: Vaccinia-Specific IgG Titers with $10^8$ Recombinant MVA in Oil and Water Emulsion Mice were immunized subcutaneously (s.c.) once (Day 0) or twice (Days 0 and 21) with $1\times10^8$ TCID$_{50}$ of a recombinant MVA-BN expressing Yellow Fever Virus (YFV) antigens alone or in emulsion (0.5 ml) with ISA720 at a W/O ratio of 30/70. Emulsion was either prepared using a single syringe and a needle or with two syringes using an I-connector. Sera were obtained 20 or 35 days post immunization and vaccinia-specific IgG antibody responses were determined by ELISA. The results are shown in FIG. 3. Unexpectedly, a greater than 10-fold increase in vaccinia-specific IgG titers was seen with the oil and water emulsions using the recombinant MVA.

Figure 4:
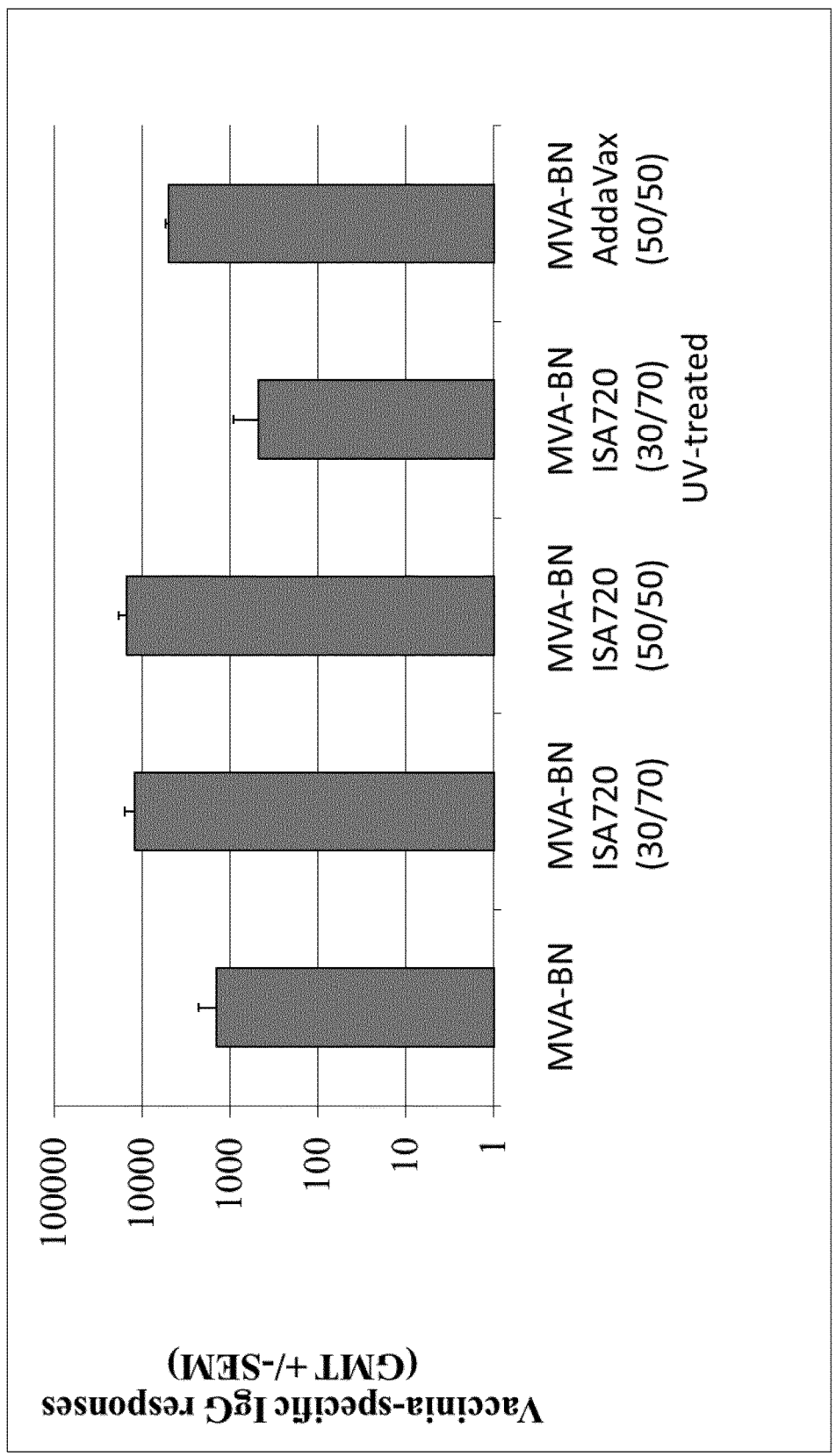
FIG. 4 depicts serum vaccinia-specific IgG antibody responses measured by ELISA after immunization with a recombinant MVA in various oil and water emulsions.

Example 10: Vaccinia-Specific IgG Titers with $10^8$ Recombinant MVA in Various Oil and Water Emulsions Mice were immunized subcutaneously (s.c.) once (Day 0) with $1\times10^8$ TCID$_{50}$ of a recombinant MVA-BN expressing respiratory syncytial virus (RSV) antigens alone or in emulsion (0.5 ml) with either ISA720 at two different W/O ratios (30/70 or 50/50) or with ADDAVAX at a 50/50 ratio. In addition one group was treated with $1\times10^8$ TCID$_{50}$ of the recombinant MVA-BN expressing respiratory syncytial virus (RSV) antigens inactivated by UV-treatment in emulsion with either ISA720 (W/O ratio 30/70) in order to determine the combined effect the live attenuated recombinant MVA-BN and oil-based adjuvant. Sera were obtained 20 days post immunization and vaccinia-specific IgG responses were determined by ELISA. The results are shown in FIG. 4. Unexpectedly, a 5 to 10-fold increase in vaccinia-specific IgG titers was seen with the oil and water emulsions using the recombinant MVA.

Figure 5:
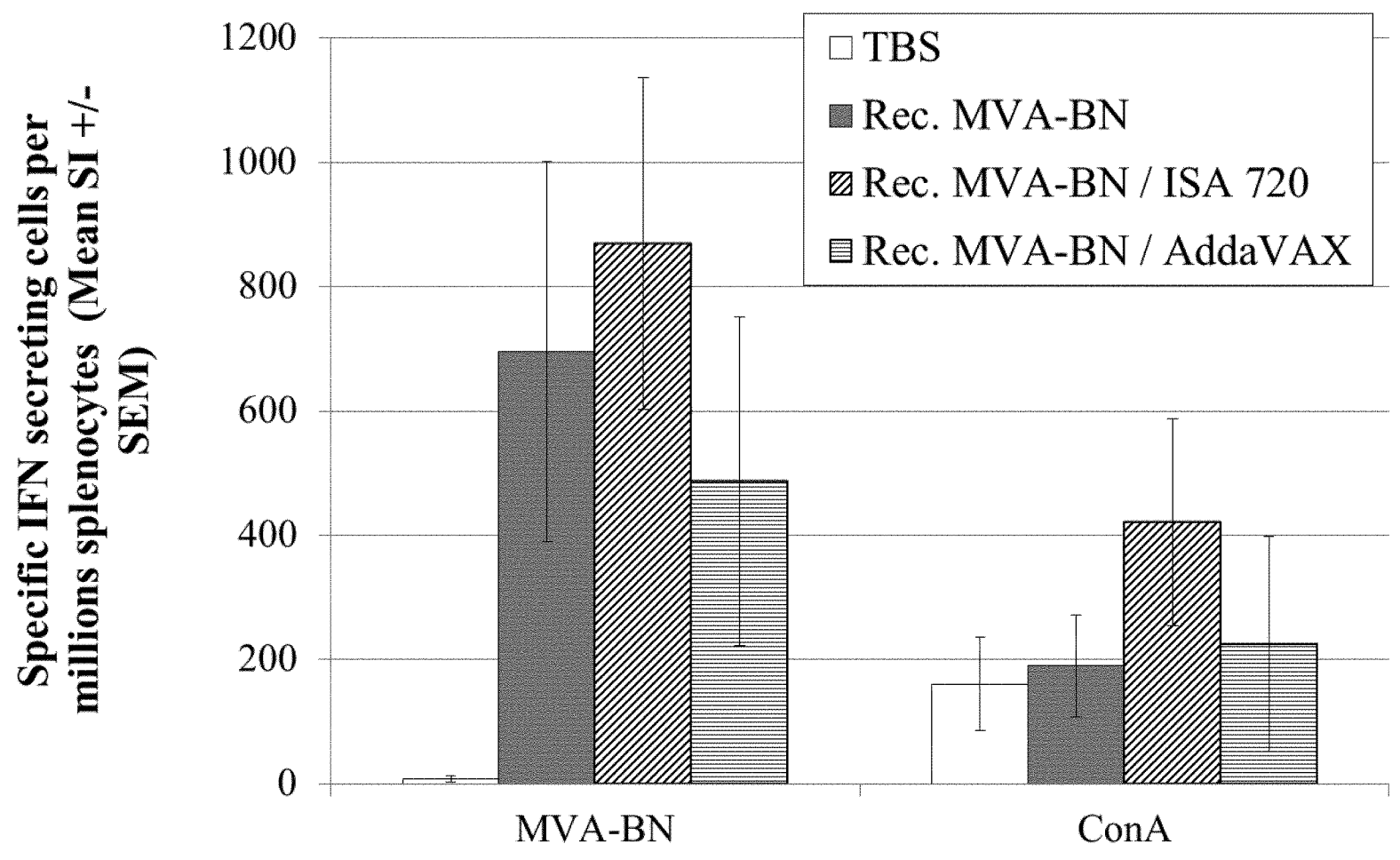

Example 11: Vaccinia-Specific T Cell Responses with $10^8$ Recombinant MVA in Various Oil and Water Emulsions Mice were immunized subcutaneously (s.c.) once (Day 0) with $1\times10^8$ TCID$_{50}$ of a recombinant MVA-BN expressing YFV antigens alone or in emulsion (0.5 ml) with ISA720 at a W/O ratio of 30/70 or ADDAVAX at a ratio 50:50. Splenocytes were isolated on Day 14 and restimulated with an MVA-specific peptide or the unspecific positive control ConA. The results are shown in FIG. 5. The oil and water emulsions did not significantly impact the T cell response to MVA-BN.

Figure 6:
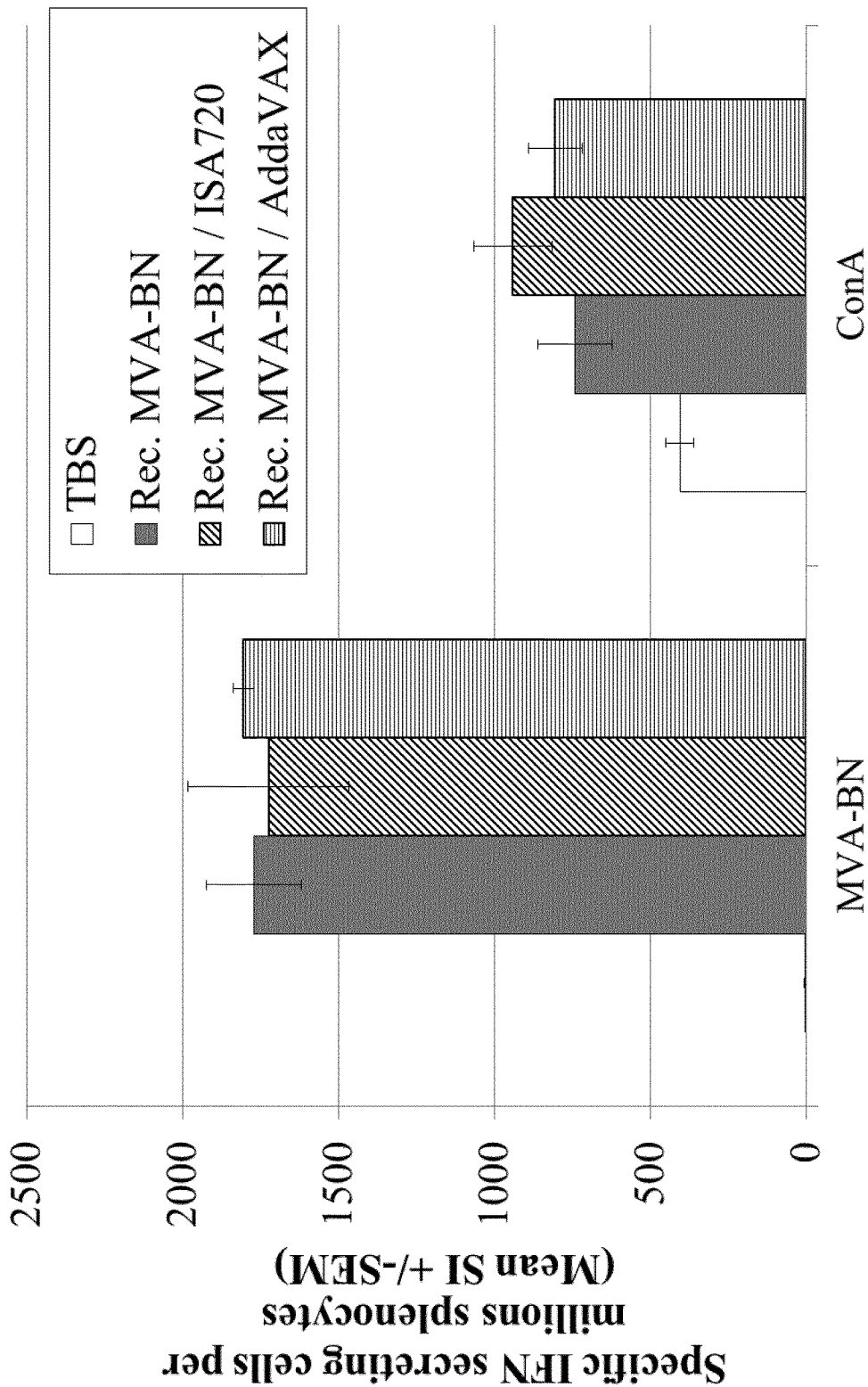
FIG. 6 depicts vaccinia-specific T cells responses measured by ELISPOT.

Example 12: Vaccinia-Specific T Cell Responses with $10^8$ Recombinant MVA in Various Oil and Water Emulsions Mice were immunized subcutaneously (s.c.) twice (Days 0 and 21) with $1\times10^8$ TCID$_{50}$ of a recombinant MVA-BN expressing YFV antigens alone or in emulsion (0.5 ml) with ISA720 at a W/O ratio of 30/70 or ADDAVAX at a ratio 50:50. Splenocytes were isolated on Day 35 and restimulated with an MVA-specific peptide or the unspecific positive control ConA. The results are shown in FIG. 6. The oil and water emulsions did not significantly impact the T cell response to MVA-BN.

Figure 7:
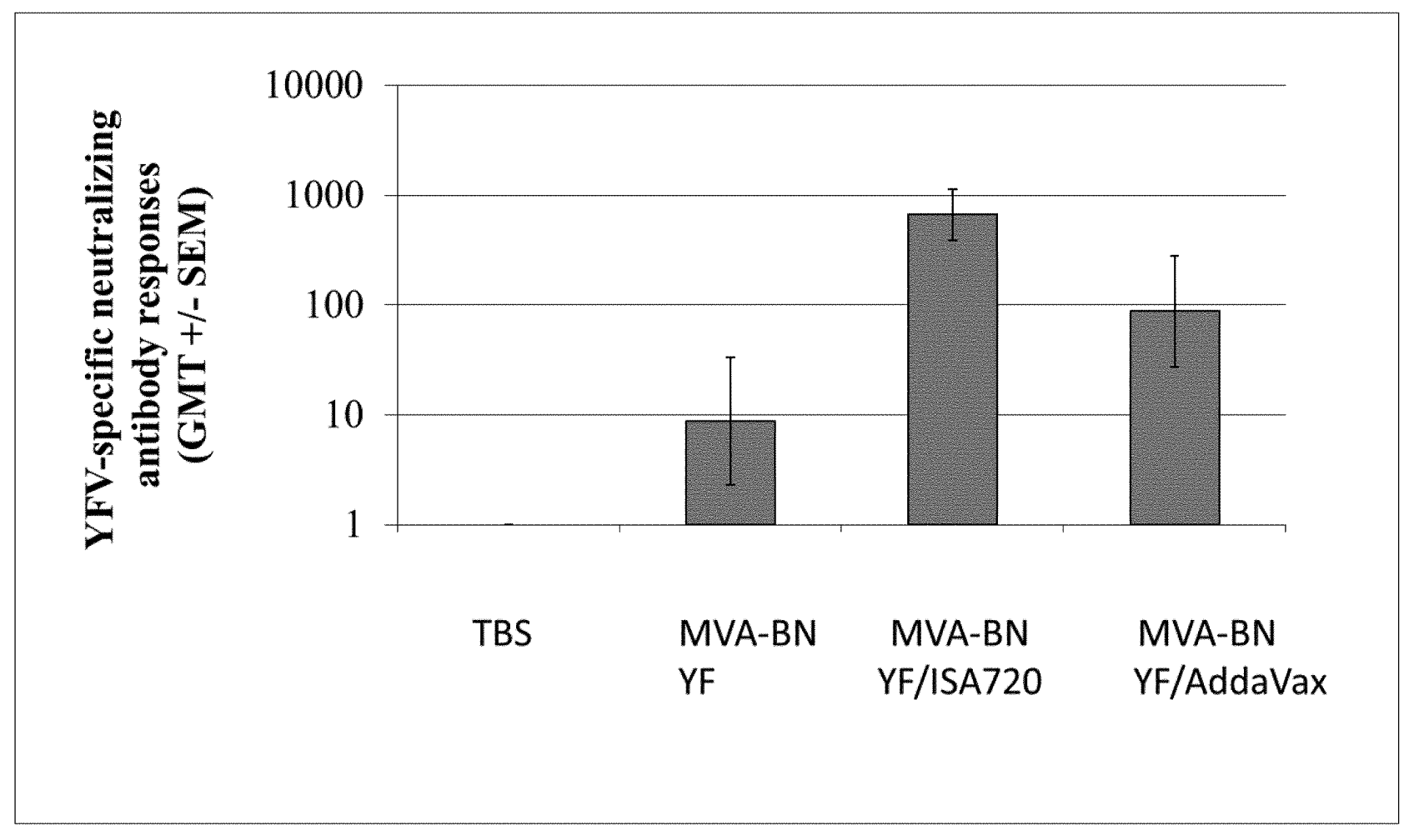

Example 13: YFV-Specific Neutralizing Antibody Responses with 108 MVA in Various Oil and Water Emulsions Mice were immunized subcutaneously (s.c.) once (Day 0) with $1\times10^8$ TCID$_{50}$ of a recombinant MVA-BN expressing YFV antigens either alone or in emulsion with ISA720 at a W/O ratio of 30/70 or with ADDAVAX at a ratio of 50:50. YFV-specific neutralizing antibody responses were determined by PRNT in sera 20 days post immunization. The results are shown in FIG. 7. Unexpectedly, YFV-specific neutralizing antibody titers were increased greater than 10-fold with the oil and water emulsions.

Figure 8:
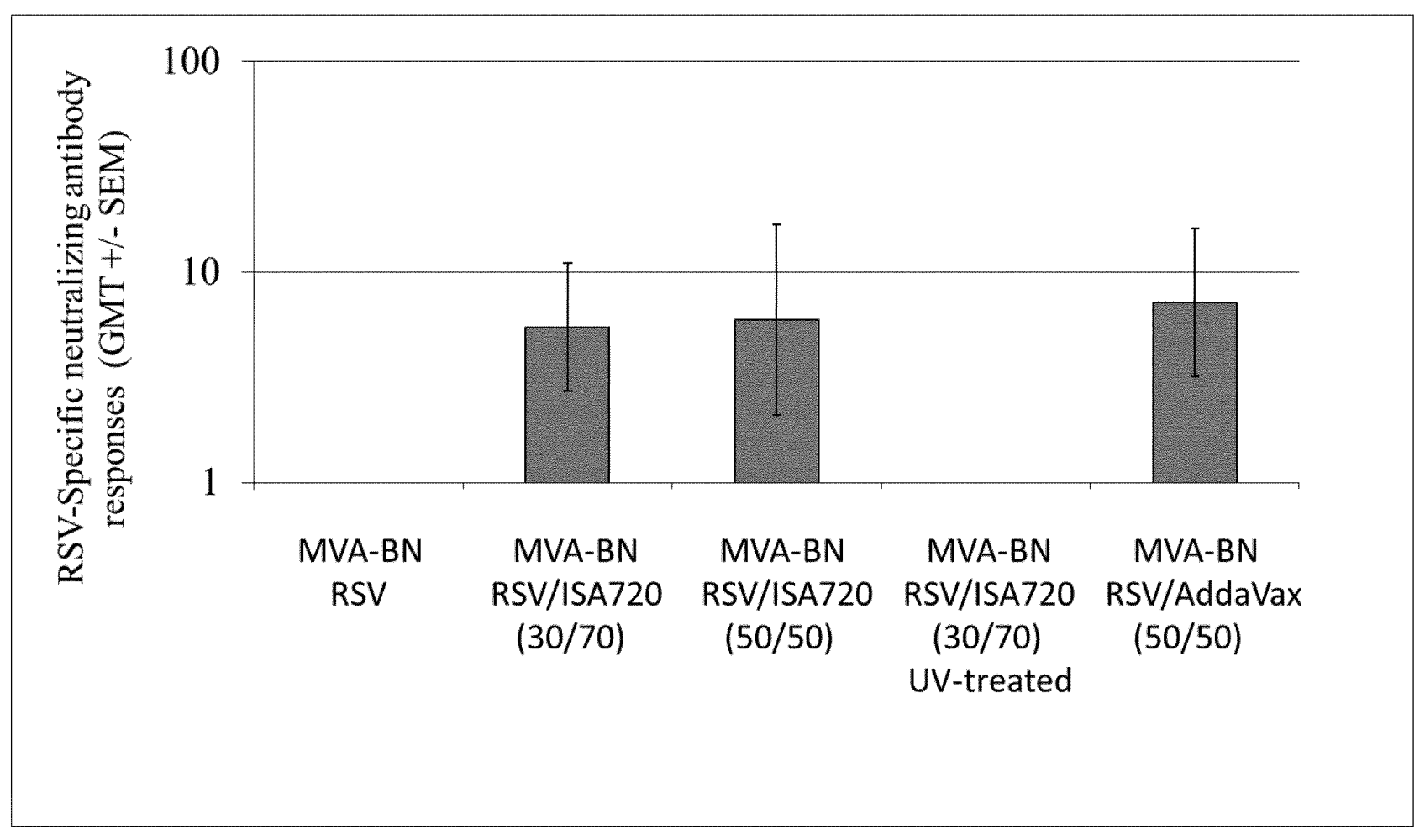

Example 14: RSV-Specific Neutralizing Antibody Responses with $10^8$ MVA in Various Oil and Water Emulsions Mice were immunized subcutaneously (s.c.) once (Day 0) with $1\times10^8$ TCID$_{50}$ of a recombinant MVA-BN expressing RSV antigens either alone or in emulsion (0.5 ml) with ISA720 at different W/O ratios (30/70 or 50:50) or with ADDAVAX at a ratio of 50:50. In addition one group was treated with $1\times10^8$ TCID$_{50}$ of the recombinant MVA-BN expressing RSV antigens inactivated by UV-treatment in emulsion with either ISA720 (W/O ratio 30/70) in order to determine the combined effect the live attenuated recombinant MVA-BN and oil-based adjuvant. RSV-specific neutralizing antibody responses were determined by PRNT in sera 20 days post immunization. The results are shown in FIG. 8. Unexpectedly, RSV-specific neutralizing antibody titers were only detected with the oil and water emulsions.

Figure 9:
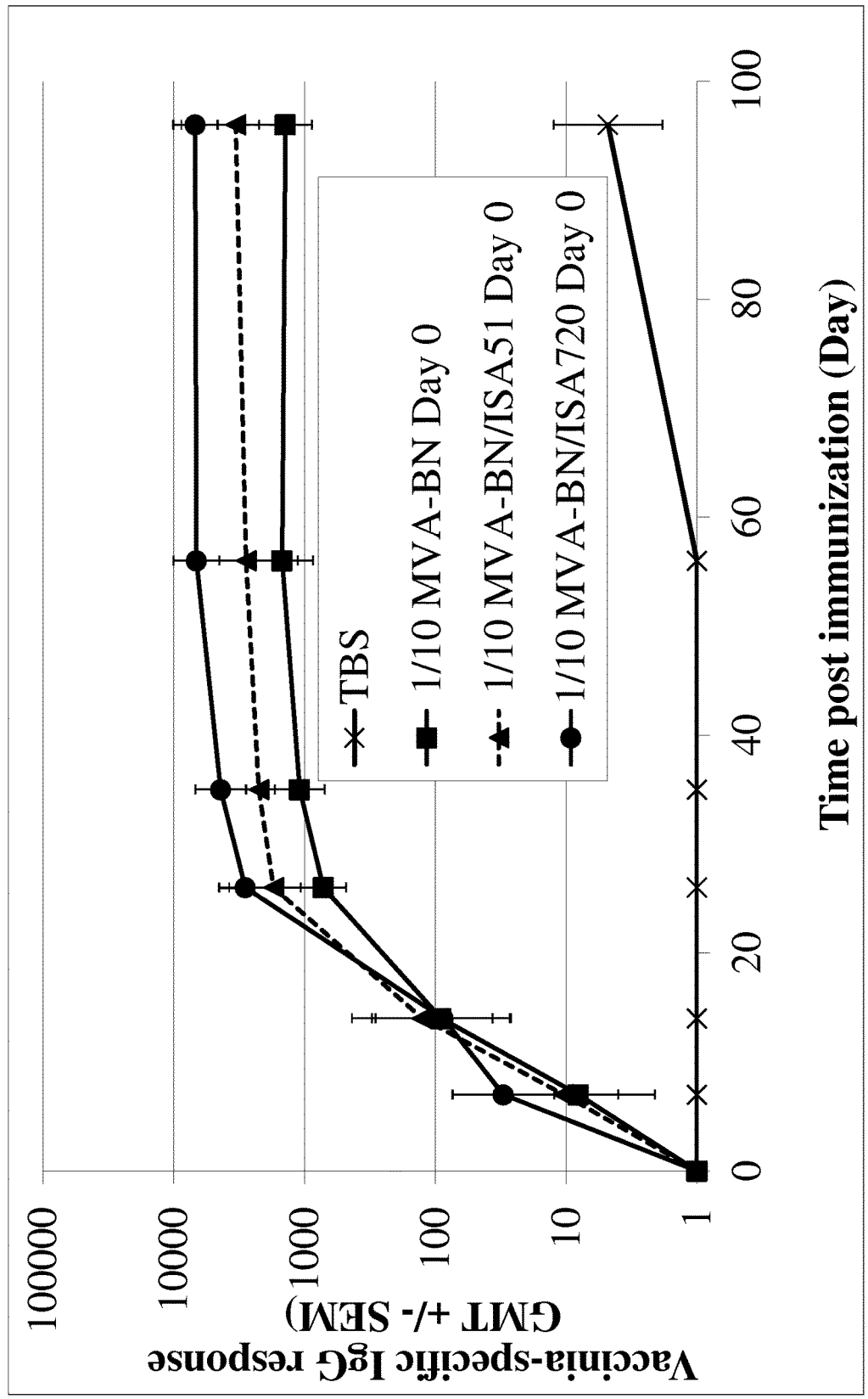
FIG. 9 depicts serum vaccinia-specific IgG responses measured by ELISA after immunization with a dose of $10^7$ non-recombinant MVA in an oil and water emulsion.

Example 15: Vaccinia-Specific IgG Titers with $10^7$ MVA in Oil and Water Emulsion Mice were immunized subcutaneously (s.c.) once (Day 0) with $1\times10^7$ TCID$_{50}$ of MVA-BN alone or in emulsion (0.05 ml) with either ISA51 or ISA720 at a ratio of 30:70 (W/O). Control mice were immunized s.c. with TBS. Sera was obtained prior the immunization and then on Days 7, 14, 26, 35, 56 and 98 post immunization. Vaccinia-specific IgG titers were determined by ELISA. The results are shown in FIG. 9. A small increase in vaccinia-specific IgG titers was seen with the oil and water emulsions.

Figure 10:
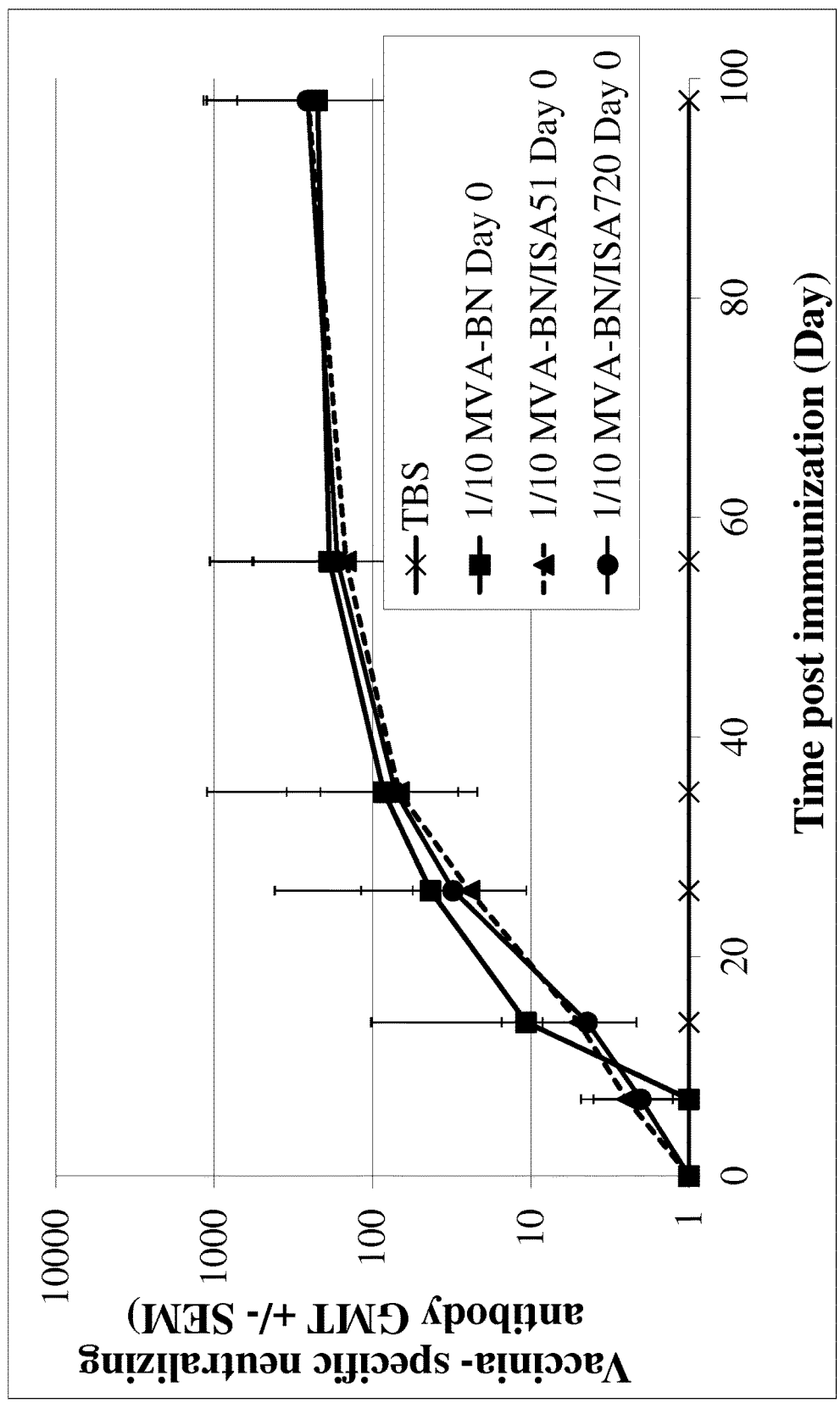
FIG. 10 depicts serum vaccinia-specific neutralizing antibody responses measured by PRNT after immunization with a dose of $10^7$ non-recombinant MVA in an oil and water emulsion.

Example 16: Vaccinia-Specific Neutralizing Antibody Responses with $10^8$ MVA in Oil and Water Emulsion Mice that were immunized subcutaneously (s.c.) once (Day 0) with $1\times10^7$ TCID$_{50}$ of MVA-BN alone or in emulsion (0.05 ml) with either ISA51 or ISA720 at a ratio of 30:70 (W/O) were analyzed for vaccinia-specific neutralizing antibody responses by PRNT. The results are shown in FIG. 10. No effect on neutralizing antibody titers was seen using $10^7$ TCID$_{50}$ of MVA-BN in an oil and water emulsion.

Example 17: Effect of Adjuvant on Immunogenicity of Different Doses of MVA

To evaluate the effect of oil e.g., MONTANIDE™ ISA720 VG adjuvant on the humoral immunogenicity on five different doses of MVA MVA-mBN294B (MVA-BN-RSV) was used as a representative example and applied subcutaneously (s.c) to adult Balb/c mice in the different doses.

Mice were vaccinated s.c. once (Day 0) with $1\times10^8$ TCID$_{50}$ MVA-mBN294B (groups 1-2), $2\times10^7$ TCID$_{50}$ MVA-mBN294B (groups 3-4), $1\times10^7$ TCID$_{50}$ MVA-mBN294B (groups 5-6), $5\times10^6$ TCID$_{50}$ MVA-mBN294B (groups 7-8) or $1\times10^6$ TCID$_{50}$ MVA-mBN294B (groups 9-10), with (groups 2, 4, 6, 8, 10) or without (groups 1, 3, 5, 7, 9) MONTANIDE™ ISA720 VG adjuvant. Blood of mice were collected one day prior to immunization (Day −1), on Days 20 and 26, and on the day of sacrifice (Day 34) and sera were prepared.

For immunization recombinant MVA-mBN294B was diluted in TBS (Tris-buffer saline, 1.21 mg/ml TRIS-(hydroxymethyl)-amino-methane, 8.18 mg/ml sodium chloride pH 7.7). 225 µl of these solutions and 525 µl of MONTANIDE™ ISA720 VG (Seppic; France) were mixed using the injection syringe to form an emulsion. 500 µl of the emulsion containing $1\times10^8$ TCID$_{50}$ MVA-mBN294B, $2\times10^7$ TCID$_{50}$, $1\times10^7$ TCID$_{50}$, $5\times10^6$ TCID$_{50}$ or $1\times10^6$ TCID$_{50}$ were injected s.c. at two sites ($2\times250$ µl) on day 0.

RSV- and vaccinia-specific IgG titers were determined in sera of Days −1, 20, 26 and 34 by ELISA to evaluate the induction of systemic immunity according to Example 4. The results are shown in FIG. 18 and Table 1 and 3.

The vaccinia-based PRNT assay as described under Example 5 was used to evaluate the level of neutralizing antibodies for groups 1 to 6. The results are shown in FIG. 19 and Table 2.

Example 18: Effect of Adjuvant on Immunogenicity of Different Doses of MVA-BN-YF in Rabbits The Vaccinia-specific IgG antibody responses in female and male rabbits after three intramuscular (i.m.) vaccinations (Days 1, 22 and 43) with MVA-BN-YF (MVA-mBN314B) with or without the oil-based adjuvant MONTANIDE™ ISA720 VG (ISA720) were analyzed.

80 Rabbits (20 per group) were vaccinated intramuscular (i.m.) 3 times 3 weeks apart (Days 1, 22 and 43) with TBS (group 1), or $2.16\times10^8$ TCID$_{50}$ MVA-mBN314B with ISA720 (group 2) or $1.08\times10^8$ TCID$_{50}$ MVA-mBN314B with ISA720 (group 3) or $3.6\times10^8$ TCID$_{50}$ MVA-mBN314B without ISA720 (group 4). Blood of rabbits were collected one week prior to immunization (Week −1), on Days 21, 42 and 70, and sera were prepared.

Figure 20:
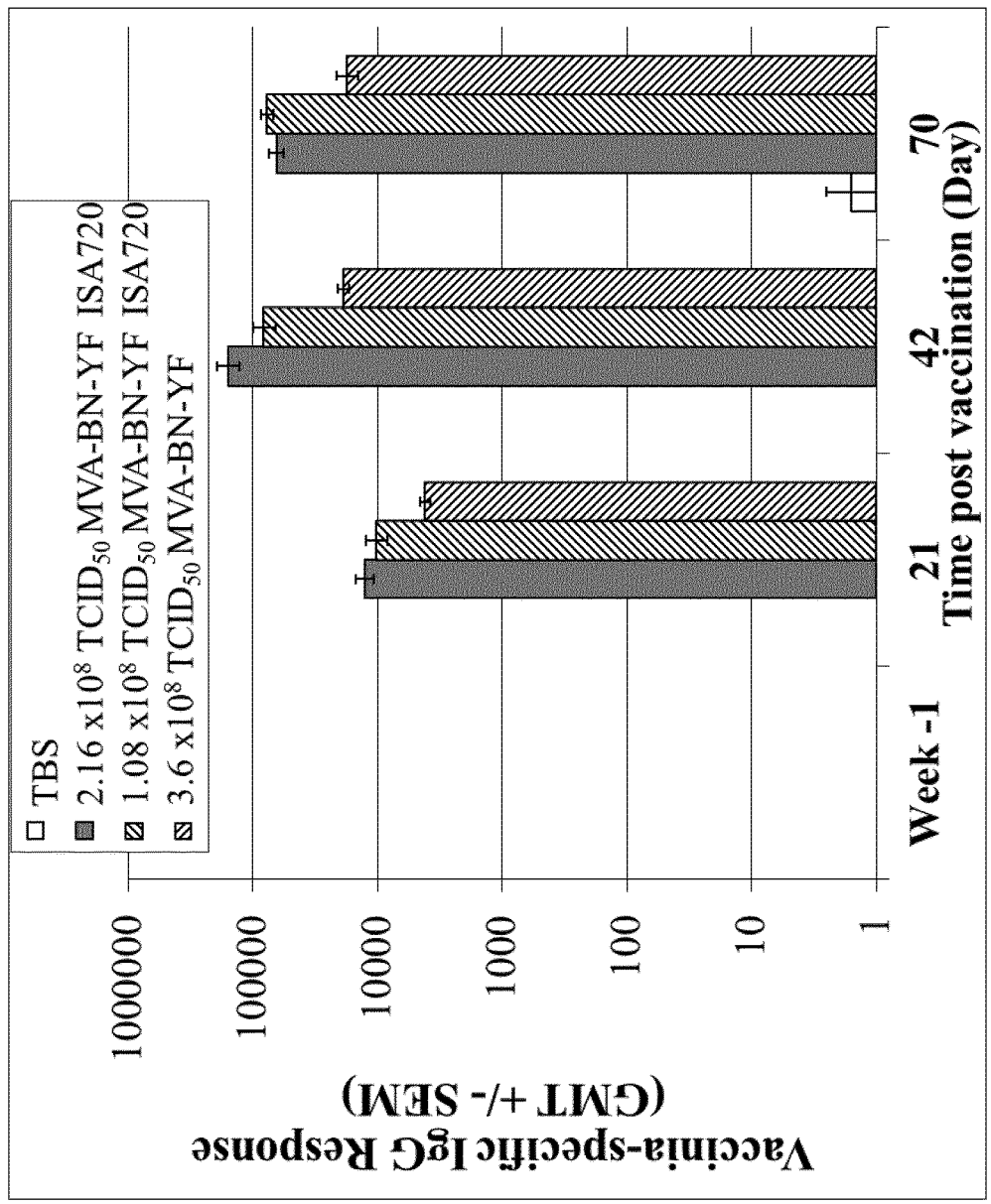
FIG. 20 depicts serum vaccinia-specific rabbit IgG responses measured by Elisa after immunization of rabbits with a dose of $2.16 \times 10^8$ TCID$_{50}$ MVA-BN-YF/ISA720, $1.08 \times 10^8$ TCID$_{50}$ MVA-BN-YF/ISA720, $3.6 \times 10^8$ TCID$_{50}$ MVA-BN-YF and TBS as a control.

For immunization recombinant MVA-mBN314B at a concentration of $7.19\times10^8$ TCID$_{50}$/ml was used. For group 2, 450 µl of this solution and 1050 µl of ISA720 were mixed using the injection syringe to form an emulsion. 1000 µl of the emulsion containing $2.16\times10^8$ TCID$_{50}$ MVA-mBN314B were injected i.m. at two sites ($2\times500$ µl) on days 1, 22 and 43. For group 3, 225 µl of this solution and 525 µl of ISA720 were mixed using the injection syringe to form an emulsion. 500 µl of the emulsion containing $1.08\times10^8$ TCID$_{50}$ MVA-mBN314B were injected i.m. at one site on days 1, 22 and 43. For group 4, 500 µl of this solution containing $3.6\times10^8$ TCID$_{50}$ MVA-mBN314B were injected i.m. at one site on days 1, 22 and 43. Rabbit serum samples were analyzed by ELISA to measure Vaccinia-specific rabbit IgG antibodies as described under Example 4. Results are shown in FIG. 20.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A pharmaceutical composition for inducing vaccinia neutralizing antibodies in an animal comprising a dose of at least $2\times10^7$ TCID$_{50}$ of a recombinant modified vaccinia Ankara (MVA) virus comprising a nucleic acid sequence encoding an antigen selected from the group consisting of:
   (a) an antigen of a yellow fever virus; and
   (b) an antigen of RSV
in an emulsion comprising oil and water, wherein the composition induces at least a 2-fold higher level of vaccinia neutralizing antibodies at 26 days after immunization when compared to the same composition in the absence of the emulsion.

2. The composition of claim 1, wherein the composition induces at least a 5-fold higher level of vaccinia neutralizing antibodies at 35 days after immunization when compared to the same composition in the absence of the emulsion.

3. The composition of claim 2, wherein the composition induces at least a 10-fold higher level of vaccinia neutralizing antibodies at 35 days after immunization when compared to the same composition in the absence of the emulsion.

4. The composition of claim 1, wherein the emulsion is a water-in-oil emulsion.

5. The composition of claim 1, wherein the emulsion is an oil-in-water emulsion.

6. The composition of claim 1, wherein the emulsion comprises mannide monooleate.

7. The composition of claim 1, wherein the emulsion comprises a mineral oil.

8. The composition of claim 1, wherein the emulsion comprises a non-mineral oil.

9. The composition of claim 7, wherein the emulsion comprises ISA 51.

10. The composition of claim 8, wherein the emulsion comprises ISA720.

11. The composition of claim 1, wherein the emulsion comprises squalene oil.

12. The composition of claim 11, wherein the emulsion comprises sorbitan trioleate.

13. The composition of claim 1 that comprises a dose of between $2\times10^7$ TCID$_{50}$ and $1.5\times10^8$ TCID$_{50}$ of said recombinant MVA.

14. The composition of claim 1, wherein the recombinant MVA comprises a nucleic acid sequence coding for an antigen of a yellow fever virus.

15. The composition of claim 13, wherein the emulsion does not additionally contain the recombinant protein encoded by the recombinant MVA.

16. The composition of claim 1, comprising a dose of at least $10^8$ TCID$_{50}$ of an MVA.

17. The composition of claim 1, wherein the MVA comprises a nucleotide sequence comprising at least one of SEQ ID NOs 1-6.

18. The composition of claim 1, wherein the animal is a human.

19. A method for inducing an immune response against a modified vaccinia Ankara (MVA) virus in an animal comprising administering to the animal a dose of at least $2\times10^7$ TCID50 of a modified vaccinia Ankara (MVA) virus comprising a nucleic acid sequence encoding an antigen selected from the group consisting of:
   (a) an antigen of a yellow fever virus; and
   (b) an antigen of RSV
in an emulsion comprising oil and water, wherein the composition induces at least a 2-fold higher level of vaccinia neutralizing antibodies at 26 days after immunization when compared to the same composition in the absence of the emulsion.

20. The method of claim 19, wherein the composition induces at least a 5-fold higher level of vaccinia neutralizing antibodies at 35 days after immunization when compared to the same composition in the absence of the emulsion.

21. The method of claim 19, wherein the emulsion comprises ISA720.

22. A pharmaceutical composition for inducing vaccinia neutralizing antibodies in an animal comprising a dose of at least $2\times10^7$ TCID$_{50}$ of a recombinant modified vaccinia Ankara (MVA) virus comprising a nucleic acid sequence encoding an antigen selected from the group consisting of:
   (a) an antigen of a yellow fever virus; and
   (b) an antigen of RSV
in an emulsion comprising oil and water,
   wherein the composition induces at least a 2-fold higher level of vaccinia neutralizing antibodies at 26 days after immunization when compared to the same composition in the absence of the emulsion inducing an immune response against a modified vaccinia Ankara (MVA) virus in an animal comprising a recombinant MVA in an oil and water emulsion, and
   wherein the emulsion does not additionally contain the recombinant protein encoded by the recombinant MVA.

23. The composition of claim 22, wherein the composition induces at least a 5-fold higher level of vaccinia neutralizing antibodies at 35 days after immunization when compared to the same composition in the absence of the emulsion.

24. The composition of claim 23, wherein the composition induces at least a 10-fold higher level of vaccinia neutralizing antibodies at 35 days after immunization when compared to the same composition in the absence of the emulsion.

25. The composition of claim 24, wherein the emulsion comprises ISA720.

26. The composition of claim 25, comprising a dose of at least $10^8$ TCID$_{50}$ of an MVA.

27. The composition of claim 23, wherein the MVA comprises a nucleotide sequence comprising at least one of SEQ ID NOs 1-6.

28. The composition of claim 26, wherein the MVA comprises a nucleotide sequence comprising at least one of SEQ ID NOs 1-5.

* * * * *

SEQUENCE LISTING

<160> NUMBER OF SEQ ID NOS: 7

<210> SEQ ID NO 1
<211> LENGTH: 900

```
<212> TYPE: DNA
<213> ORGANISM: Artificial Sequence
<220> FEATURE:
<223> OTHER INFORMATION: synthetic construct - codon optimized

<400> SEQUENCE: 1
atgagcaaga acaaggacca gcggaccgcc aagaccctgg aacggacctg ggacaccctg      60
aaccatctgc tgttcatcag tagctgcctg tacaagctga acctgaagtc cgtggcccag     120
atcaccctga gcatcctggc catgatcatc agcaccagcc tgatcattgc cgccatcatc     180
tttatcgcca gcgccaacca caaagtgacc cccaccacag ccatcatcca ggacgccacc     240
tcccagatca gaacaccac ccccacctac ctgacccaga accctcagct gggcatcagc     300
cccagcaacc ccagcgagat caccagccag atcacaacca tcctggcctc caccacccct     360
ggcgtgaagt ccaccctgca gagcaccacc gtgaaaacca gaataccac accacacag      420
acccagccca gcaagcccac caccaagcag agacagaaca gcccccctc caagcccaac     480
aacgacttcc acttcgaggt gttcaacttc gtgccctgca gcatctgcag caacaacccc     540
acctgttggg ccatctgcaa gcggatcccc aacaagaagc ccggcaagaa accacaacc     600
aagcctacca agaagcctac cctgaaaaacc accaagaagg accccaagcc ccagaccacc     660
aagagcaaag aggtgccaac caccaagccc accgaggaac ccaccatcaa caccaccaag     720
accaacatca tcaccaccct gctgacctcc aacaccaccg caaccccga gctgacaagc     780
cagatggaaa ccttccacag caccagcagc gagggcaacc ctagccctag ccaggtgtcc     840
accacctccg agtacccag ccagcctagc agccccccca cacccccag acagtgataa     900

<210> SEQ ID NO 2
<211> LENGTH: 879
<212> TYPE: DNA
<213> ORGANISM: Artificial Sequence
<220> FEATURE:
<223> OTHER INFORMATION: synthetic construct - codon optimized

<400> SEQUENCE: 2
atgtccaagc acaagaatca gagaacagcc cggacactgg aaaagacatg ggatacactc      60
aatcacctga tcgtgatcag ctcctgtctc taccggctca acctcaagag cattgcccag     120
attgccctgt ccgtgctggc aatgattatt ccactagtc tcattatcgc tgctattatc     180
ttcatcatta gtgccaatca taagtcacc ctcacaaccg tcaccgtgca gaccattaaa     240
aaccataccg agaagaatat ctcaacatat ctgacacagg tcccccccga agagtgaac      300
tcttccaaac agcccacaac cacctccccc attcatacca atagtgccac aatttctccc     360
aacacaaagt ctgaaacaca ccacactact gctcagacaa agggccgaat caccacctct     420
actcagacca ataagccatc aacaaaatcc cgctccaaaa acccacctaa aaaacctaaa     480
gatgactatc atttcgaagt ctttaattc gtcccatgtt ccatttgcgg aaacaaccag     540
ctctgtaaat ctatctgtaa accatcccc tctaacaagc aaaaaagaa acctactatt     600
aaaccaacta ataagcccac cactaagact actaacaaac gcgatccaaa acacccgcc      660
aaaatgccta aaaagagat cattacaaac ccagccaaga aaccaactct caaaactacc     720
gaacgggaca cctccatttc tcagtctacc gtgctcgata ccatcactcc caaatacact     780
atccagcagc agtcactcca ctcaacaacc tccgagaaca cccctcctc aacccagatt     840
cctactgctt ccgaaccatc cacctcaac cccaattga                             879

<210> SEQ ID NO 3
```

<211> LENGTH: 1806
<212> TYPE: DNA
<213> ORGANISM: Artificial Sequence
<220> FEATURE:
<223> OTHER INFORMATION: synthetic construct - codon optimized

<400> SEQUENCE: 3

| | | | | | |
|---|---|---|---|---|---|
| atggccctga | gcaaagtgaa | gctgaacgac | accctgaaca | aggaccagct | gctgtccagc | 60 |
| tccaagtaca | ccatccagag | aagcaccggc | acagcatcg | acaccccaa | ctacgacgtg | 120 |
| cagaagcaca | tcaataagct | gtgcggcatg | ctgctgatca | ccgaggacgc | caaccacaag | 180 |
| ttcaccggcc | tgatcgggat | gctgtacgcc | atgagccggc | tgggccggga | ggacaccatc | 240 |
| aagatcctgc | gggacgccgg | ctaccacgtg | aaggccaacg | gcgtggacgt | gaccacccac | 300 |
| cggcaggaca | tcaacggcaa | agaaatgaag | ttcgaggtgc | tgaccctggc | cagcctgacc | 360 |
| accgagatcc | agatcaacat | cgagatcgag | agccggaagt | cctacaagaa | aatgctgaaa | 420 |
| gaaatgggcg | aggtggcccc | cgagtacaga | cacgacagcc | ccgactgcgg | catgatcatc | 480 |
| ctgtgtatcg | ccgccctggt | catcacaaag | ctggccgctg | cgacagatc | tggcctgacc | 540 |
| gccgtgatca | gacgggccaa | caacgtgctg | aagaacgaga | tgaagcggta | caagggcctg | 600 |
| ctgcccaagg | atatcgccaa | cagcttctac | gaggtgttcg | aaaagcaccc | ccacttcatc | 660 |
| gacgtgttcg | tgcacttcgg | cattgcccag | agcagcacca | gaggcggcag | cagagtggag | 720 |
| ggcatcttcg | ccggcctgtt | catgaacgcc | tacggcgctg | ccaggtcat | gctgagatgg | 780 |
| ggcgtgctgg | ccaagagcgt | gaagaacatc | atgctgggcc | acgccagcgt | gcaggccgag | 840 |
| atggaacagg | tggtggaggt | gtacgagtac | gcccagaagc | tgggcggcga | ggccggcttc | 900 |
| taccacatcc | tgaacaaccc | caaggcctcc | ctgctgtccc | tgacccagtt | cccccacttt | 960 |
| agcagcgtgg | tgctcggaaa | tgcagccgga | ctgggcatca | tgggcgagta | ccgcggcacc | 1020 |
| cccagaaacc | aggacctgta | cgacgccgcc | aaggcctacg | ccgagcagct | gaaagaaaac | 1080 |
| ggcgtgatca | actacagcgt | gctggacctg | acagccgagg | aactgaagc | cattaagcac | 1140 |
| cagctgaacc | ctaaggacaa | cgacgtggag | ctgaacttcg | atctgctgaa | actggccggc | 1200 |
| gacgtggaaa | gcaaccctgg | ccccagcaga | cggaacccct | gcaagttcga | gatccggggc | 1260 |
| cactgcctga | acggcaagcg | gtgccacttc | agccacaact | acttcgagtg | gcccctcat | 1320 |
| gctctgctgg | tccggcagaa | ctttatgctg | aaccggatcc | tgaagtccat | ggacaagagc | 1380 |
| atcgatacc | tgagcgagat | cagcggagcc | gccgaactgg | atagaaccga | ggaatacgcc | 1440 |
| ctgggcgtgg | tcggagtgct | ggaaagctac | atcggcagca | tcaacaacat | caccaagcag | 1500 |
| agcgcctgcg | tggccatgag | caagctgctg | accgagctga | cagcgacga | tatcaagaag | 1560 |
| ctgcgcgaca | acgaagaact | gaactccccc | aagatccggg | tgtacaacac | agtgatcagc | 1620 |
| tacattgaga | gcaaccggaa | gaacaacaag | cagaccatcc | atctgctgaa | gcggctgccc | 1680 |
| gccgacgtgc | tgaaaagac | catcaagaac | accctggaca | tccacaagtc | catcaccatc | 1740 |
| aataaccccca | aagaaagcac | cgtgtccgac | accaacgacc | acgccaagaa | caacgacacc | 1800 |
| acctga | | | | | | 1806 |

<210> SEQ ID NO 4
<211> LENGTH: 1725
<212> TYPE: DNA
<213> ORGANISM: Artificial Sequence
<220> FEATURE:
<223> OTHER INFORMATION: synthetic construct - codon optimized

<400> SEQUENCE: 4

```
atggaactcc ctattctcaa agccaatgct attactacca ttctcgccgc tgtcacctttt    60 tgtttcgcct cttcccagaa tattaccgaa gagttttacc agtctacctg ttccgccgtc   120
agtaaaggat acctgtccgc cctccgcact ggttggtata ctagtgtcat tacaatcgaa   180
ctctcaaata taaagaaaa taagtgtaat gggaccgatg ctaaagtcaa actcattaaa   240
caagaactcg ataagtataa gaatgctgtc actgagctgc aactgctgat gcagtctaca   300
cccgcagcca ataatcgagc cagacgcgag ctgcctcgct ttatgaatta tactctcaat   360
aatactaaaa agacaaacgt caccctcagt aaaagcgaa aagacggtt tctcggattc     420 ctcctcggcg tgggctctgc tatcgctagc ggaattgctg tctccaaagt cctccatctg   480 gaagggagg tcaacaaaat taagtctgct ctcctctcta caaacaaag cgtcgtgtct    540 ctctccaatg gcgtgtctgt gctcacctct aaagtgctcg acctcaaaaa ttacattgat   600
aaacagctgc tccctattgt gaacaaacag tcttgccgca ttagcaatat cgaaaccgtc   660
attgaatttc aacaaagaa taataggctc ctcgaaatta cccgcgaatt ctccgtgaat    720
gtgggagtca acacctgt ctctacctat atgctcacta actccgaact cctctcccttc   780 attaacgata tgcccattac aaatgatcag aaaaaactca tgtctaataa cgtccagatt   840
gtccgccagc agtcttatag cattatgtcc attatcaaag aggaagtcct cgcttacgtc   900
gtccagctcc ctctgtatgg ggtcatcgat acaccttgtt ggaaactcca tacctcccca   960
ctgtgtacaa ccaataccaa agaagggtcc aatatttgcc tgacaagaac cgaccgcggg  1020
tggtactgtg ataatgccgg ctctgtctcc ttttttcccc aggccgaaac ctgtaaagtc  1080
cagtctaatc gagtctttg cgatactatg aattccctca ccctccttc agaagtgaat    1140 ctctgtaacg tcgatatttt caaccctaaa tatgattgca aaattatgac cagtaaaact   1200
gacgtgtcct cttccgtcat caccctccctc ggtgctattg tgtcttgtta cggaaaaact   1260
aaatgcacgg ctagtaataa gaaccgaggc attattaaga cctttttccaa cggctgtgat  1320 tatgtgtcta caaaggcgt ggatactgtc agtgtcggaa atacactcta ctatgtcaac    1380
aaacaggaag ggaaaagtct ctacgtcaaa gggagccga taatcaattt ttacgatccc   1440
ctcgtctttc cctccgatga atttgatgcc agtatttccc aggtgaacga aaaaatcaat   1500
cagtccctcg cttttattag aaaatctgat gaactcctgc ataatgttaa cgctggcaag   1560
agtaccacaa acatcatgat caccaccatc atcatcgtga tcattgtgat cctgctgagt   1620
ctgatcgccg tgggcctgct gctgtactgc aaggcccgca gcacccctgt gaccctgtcc   1680
aaggatcagc tgtccggcat caacaatatc gccttctcca actga              1725
```

<210> SEQ ID NO 5
<211> LENGTH: 2037
<212> TYPE: DNA
<213> ORGANISM: Artificial Sequence
<220> FEATURE:
<223> OTHER INFORMATION: synthetic construct - codon optimized

<400> SEQUENCE: 5

```
atgagccacg acgtgctgac cgtgcagttc ctgatcctgg gcatgctgct gatgacaggc    60
ggcgtgacac tcgtgcggaa gaacagatgg ctgctgctga cgtgaccag cgaggacctg   120 ggcaagacct tctctgtggg caccggcaac tgcaccacca acatcctgga agccaagtac   180
tggtgccccg acagcatgga gtacaactgc cccaacctga gccccagaga ggaacccgac   240
gacatcgact gctggtgcta cggcgtggaa aacgtgcggg tggcctacgg caagtgcgat   300
```

-continued

```
agcgccggca gaagcagaag aagcaggcgg gccatcgacc tgcccaccca cgaaaaccac        360
ggcctgaaaa cccggcagga aaagtggatg accggccgga tgggcgagcg gcagctgcag        420
aaaattgagc ggtggtttgt gcggaacccc ttcttcgccg tgaccgccct gacaatcgcc        480
tacctcgtgg gcagcaacat gacccagaga gtcgtgatcg ccctgctggt gctggctgtg        540
ggccctgcct atagcgccca ctgtatcggc atcaccgacc gggacttcat cgagggcgtg        600
cacggcggaa catgggtgtc cgctaccctg aacaggata agtgcgtgac cgtgatggcc        660
cccgacaagc ccagcctgga catcagcctg gaaaccgtgg ccatcgatag acccgccgaa        720
gtgcggaaag tgtgctacaa cgccgtgctg acacacgtga agatcaacga caagtgcccc        780
agcaccggcg aagcccacct ggccgaagag aacgagggcg acaacgcctg caagcggacc        840
tacagcgata gaggctgggg caatggctgc ggcctgtttg caagggcag catcgtggcc         900 tgcgccaagt tcacctgtgc caagagcatg agcctgttcg aggtggacca gaccaagatc        960
cagtacgtga tccgggccca gctgcacgtg ggagccaagc aggaaaactg gaacaccgac       1020
atcaagaccc tgaagttcga cgccctgagc ggctcccagg aagtggaatt catcggctat       1080
ggcaaggcca ccctggaatg ccaggtgcag accgccgtgg acttcggcaa cagctatatc       1140
gccgagatgg aaaccgagag ctggatcgtg accggcagt gggctcagga tctgaccctg       1200
ccttggcagt ctggctctgg cggagtgtgg cgggaaatgc caccctggt ggaattcgag        1260 cctcccacg ccgccaccat tagagtgctg gccctgggca atcaggaagg ctctctgaaa        1320
acagccctga ccggcgccat gagagtgacc aaggacacca cgacaacaa cctgtacaag        1380 ctgcatggcg ccacgtgtc ctgcagagtg aagctgtctg ccctgacact gaagggcacc        1440
agctacaaga tctgcaccga caagatgttc ttcgtgaaga accccaccga caccggccac       1500
ggcacagtcg tgatgcaagt gaaggtgtcc aagggcgctc cctgccggat ccctgtgatc       1560
gtggccgatg atctgacagc cgccatcaac aagggcatcc tcgtgacagt gaaccctatc       1620
gcctccacca cgatgacga ggtgctgatc gaagtgaacc cccccttcgg cgactcctac       1680
atcatcgtgg acggggcga cagcagactg acctaccagt ggcacaaaga gggcagcagc       1740
atcggcaagc tgttcaccca gaccatgaag ggcgtggaac ggctggccgt gatgggagat       1800
accgcctggg atttcagcag cgctggcggc ttctttacca gcgtgggcaa gggaatccac       1860
accgtgttcg gcagcgcctt ccagggactg ttcggcggcc tgaactggat caccaaagtg       1920
atcatgggcg ctgtgctgat ctgggtggga atcaacaccc ggaacatgac catgagcatg       1980
tccatgatcc tcgtgggagt gattatgatg ttcctgtccc tgggcgtggg cgcctga         2037
```

```
<210> SEQ ID NO 6
<211> LENGTH: 108
<212> TYPE: DNA
<213> ORGANISM: Artificial Sequence
<220> FEATURE:
<223> OTHER INFORMATION: Promoter sequence

<400> SEQUENCE: 6
```

```
taaaaattga aaataaatac aaaggttctt gagggttgtg ttaaattgaa agcgagaaat         60
aatcataaat aatttcatta tcgcgatatc cgttaagttt gtatcgta                    108
```

```
<210> SEQ ID NO 7
<211> LENGTH: 9
<212> TYPE: PRT
<213> ORGANISM: Artificial Sequence
<220> FEATURE:
<223> OTHER INFORMATION: F2L 26-34  peptide
```

```
<400> SEQUENCE: 7

Ser Pro Tyr Ala Ala Gly Tyr Asp Leu
1               5
```